US009198971B2

(12) United States Patent
Soula

(10) Patent No.: US 9,198,971 B2
(45) Date of Patent: Dec. 1, 2015

(54) INJECTABLE SOLUTION AT PH 7 COMPRISING AT LEAST ONE BASAL INSULIN THE PI OF WHICH IS BETWEEN 5.8 AND 8.5 AND A SUBSTITUTED CO-POLYAMINO ACID

(71) Applicant: ADOCIA, Lyons (FR)

(72) Inventor: Olivier Soula, Meyzieu (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 13/737,353

(22) Filed: Jan. 9, 2013

(65) Prior Publication Data

US 2013/0178415 A1    Jul. 11, 2013

Related U.S. Application Data

(60) Provisional application No. 61/584,625, filed on Jan. 9, 2012, provisional application No. 61/584,623, filed on Jan. 9, 2012.

(30) Foreign Application Priority Data

Jan. 9, 2012 (FR) ..................... 12 50223
Jan. 9, 2012 (FR) ..................... 12 50224

(51) Int. Cl.
| | |
|---|---|
| A61K 38/28 | (2006.01) |
| A61K 47/42 | (2006.01) |
| A61K 47/34 | (2006.01) |
| A61K 38/26 | (2006.01) |
| A61K 9/00 | (2006.01) |
| A61K 45/06 | (2006.01) |
| A61K 47/30 | (2006.01) |
| A61K 9/08 | (2006.01) |

(52) U.S. Cl.
CPC ............... *A61K 47/34* (2013.01); *A61K 9/0019* (2013.01); *A61K 9/08* (2013.01); *A61K 38/26* (2013.01); *A61K 38/28* (2013.01); *A61K 45/06* (2013.01); *A61K 47/30* (2013.01); *A61K 47/42* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2,387,201 | A | 10/1945 | Weiner |
| 4,826,818 | A | 5/1989 | Mori et al. |
| 5,656,722 | A | 8/1997 | Dörschug |
| 6,100,376 | A | 8/2000 | Dörschug |
| 7,226,618 | B1 | 6/2007 | Touraud et al. |
| 7,718,609 | B2 | 5/2010 | Steiner et al. |
| 8,426,382 | B2 | 4/2013 | Soula et al. |
| 2003/0225033 | A1 | 12/2003 | Groman et al. |
| 2006/0099264 | A1* | 5/2006 | Chan et al. ............... 424/486 |
| 2006/0188555 | A1* | 8/2006 | Cormier et al. ........... 424/448 |
| 2007/0196497 | A1 | 8/2007 | Pouliquen et al. |
| 2008/0014250 | A1 | 1/2008 | Soula et al. |
| 2008/0026070 | A1* | 1/2008 | Bonnet-Gonnet ......... 424/489 |
| 2008/0039368 | A1 | 2/2008 | Steiner et al. |
| 2009/0011028 | A1* | 1/2009 | Checot et al. ............. 424/486 |
| 2009/0048412 | A1 | 2/2009 | Soula et al. |
| 2009/0110742 | A1* | 4/2009 | Constancis et al. ....... 424/499 |
| 2009/0304665 | A1 | 12/2009 | Frost et al. |
| 2010/0069292 | A1 | 3/2010 | Pohl et al. |
| 2010/0167984 | A1 | 7/2010 | Soula et al. |
| 2010/0167991 | A1 | 7/2010 | Soula et al. |
| 2010/0249020 | A1 | 9/2010 | Soula et al. |
| 2011/0172166 | A1 | 7/2011 | Charvet et al. |
| 2011/0178011 | A1 | 7/2011 | Soula et al. |
| 2011/0195913 | A1 | 8/2011 | Charvet et al. |
| 2011/0212901 | A1 | 9/2011 | Akiyoshi et al. |
| 2012/0295833 | A1 | 11/2012 | Charvet et al. |
| 2012/0309680 | A1 | 12/2012 | Charvet et al. |
| 2013/0065826 | A1 | 3/2013 | Soula et al. |
| 2014/0187499 | A1 | 7/2014 | Soula et al. |
| 2014/0378373 | A2 | 12/2014 | Soula et al. |
| 2015/0025005 | A1 | 1/2015 | Langer et al. |

FOREIGN PATENT DOCUMENTS

| | | | | |
|---|---|---|---|---|
| AU | 2007/255367 | * | 12/2007 | ............... A61K 9/00 |
| EP | 1 222 926 | | 7/2002 | |
| EP | 2 360 188 A1 | | 8/2011 | |
| EP | 2 387 989 A2 | | 11/2011 | |
| FR | 2 801 226 A1 | | 5/2001 | |
| FR | 2 840 614 A1 | | 12/2003 | |
| FR | 2 862 536 A1 | | 5/2005 | |
| FR | 2 985 428 A1 | | 7/2013 | |
| FR | 2 985 429 A1 | | 7/2013 | |

(Continued)

OTHER PUBLICATIONS

McKeage and Goa, Insulin Glargine A Review of its Therapeutic Use as a Long-Acting Agent for the Management of Type 1 and 2 Diabetes Mellitus, Drugs 2001:61(1):1599-1624.*

Cengiz et al., "Early Pharmacokinetic and Pharmacodynamic Effects of Mixing Lispro With Glargine Insulin," *Diabetes Care*, vol. 33, No. 5, pp. 1009-1012, May 2010.

Abstract of Testa et al., "Patient Satisfaction, Quality of Life and Glycemic Variability in Type 1 and 2 Diabetes: A Cross-Over Trial of Insulin Glargine + Glulisine vs Premix Analog Insulin," www.Professional.Diabetes.org, Abstract No. 2163-PO, 2010.

(Continued)

*Primary Examiner* — Karlheinz R Skowronek
*Assistant Examiner* — Joseph Fischer
(74) *Attorney, Agent, or Firm* — Oliff PLC

(57) ABSTRACT

The invention relates to a composition in the form of an injectable aqueous solution, the pH of which is between 6.0 and 8.0, comprising at least:
  a) a basal insulin, the isoelectric point pI of which is between 5.8 and 8.5;
  b) a co-polyamino acid bearing carboxylate charges and substituted with hydrophobic radicals.
In one embodiment, the compositions according to the invention also comprise a prandial insulin and/or gut hormone.

30 Claims, 1 Drawing Sheet

(56) References Cited

FOREIGN PATENT DOCUMENTS

| WO | WO 03/053339 A2 * | 7/2003 |
|---|---|---|
| WO | WO 2004/060968 A1 | 7/2004 |
| WO | WO 2004/096854 A2 | 11/2004 |
| WO | 2006/051103 A2 | 5/2006 |
| WO | WO 2007/116143 A1 | 10/2007 |
| WO | WO 2007/121256 A2 | 10/2007 |
| WO | WO 2007/141344 A2 | 12/2007 |
| WO | WO 2008/030119 A1 | 3/2008 |
| WO | WO 2009/021955 A1 | 2/2009 |
| WO | WO 2009/063072 A2 | 5/2009 |
| WO | 2010/028055 A1 | 3/2010 |
| WO | WO 2010/041138 A2 | 4/2010 |
| WO | WO 2010/053140 A1 | 5/2010 |
| WO | WO 2010/056403 A1 | 5/2010 |
| WO | WO 2010/122385 A1 | 10/2010 |
| WO | WO 2011/077405 A1 | 6/2011 |
| WO | WO 2011/098962 A2 | 8/2011 |
| WO | WO 2011/144673 A2 | 11/2011 |
| WO | WO 2011/144676 A1 | 11/2011 |
| WO | WO 2011/147980 A1 | 12/2011 |
| WO | WO 2012/153070 | 11/2012 |
| WO | WO 2013/021143 A1 | 2/2013 |
| WO | WO 2013/104861 A1 | 7/2013 |

OTHER PUBLICATIONS

Asbtract of Testa et al., "Decreased Glycemic Variability during Insulin Therapy Improves Patient-Centered Outcomes in Type 1 and 2 Diabetes," www.Professional.Diabetes.org, Abstract No. 1-LB, 2010.
Uehata et al., "Effect of sulfobutyl ether-β-cyclodextrin on bioavailability of insulin glargine and blood glucose level after subcutaneous injection to rats," *International Journal of Pharmaceutics*, pp. 1-6, 2011.
Deming, "Polypeptide and Polypeptide Hybrid Copolymer Synthesis via NCA Polymerization," *Adv Polm Sci*, vol. 202, pp. 1-18, 2006.
Deming, "Facile synthesis of block copolypeptides of defined architecture," *Nature*, vol. 390, pp. 386-389, Nov. 27, 1997.
Lu et al., "Hexamethyldisilazane-Mediated Controlled Polymerization of α-Amino Acid N-Carboxyanhydrides," *J. Am. Chem. Soc.*, vol. 129, pp. 14114-14115, 2007.
Lu et al., "N-Trimethylsilyl Amines for Controlled Ring-Opening Polymerization of Amino Acid N-Carboxyanhydrides and Facile End Group Functionalization of Polypeptides," *J. Am. Chem. Soc.*, vol. 130, pp. 12562-12563, 2008. (with supporting Information pp. S1-S8).
Huile et al., "Controlled Release of Insulin From Nanoparticles of Amphiphilic Block Copolyamino Acid," *Journal of Controlled Release*, vol. 64, pp. 319-321, 2000.
"Patients in Pivotal Study Achieved Better Glycemic Control Without Weight Gain or Increased Hypoglycemia Risk Versus Insulin Glargine," *Lilly*, XP-002686281, Oct. 19, 2011.
Abstract of Cengiz et al., "Should We Mix Lispro with Glargine? Removing the Guesswork by Euglycemic Clamp Studies," www.Professional.Diabetes.org, Abstract No. 19-OR, 2009.
"Highlights of Prescribing Information" for Lantus, *Sanofi-Aventis US LLC.*, 2009.
Draft Prescribing Information Concerning Lantus®; Apr. 20, 2000; pp. 1-14.
International Search Report dated Dec. 3, 2012 issued in International Application No. PCT/FR2012/051880.
Sanchez-Chaves et al., "Poly (vinyl alcohol) functionalized by monosuccinate groups. Coupling of bioactive amino compounds," Polymer, 1998, pp. 2751-2757, vol. 39, No. 13.
French Search Report issued in French Application No. 1157291 dated Mar. 23, 2012 (w/translation).
Dubowchik et al.; "Improved Cytotoxicity of Antitumor Compounds Deliverable by the LDL Pathyway[1,2];" *Bioconjugate Chem.*; 1995; pp. 427-439; vol. 6.
Smoot et al.; "Oligosaccharide Synthesis: From Conventional Methods to Modern Expeditious Strategies;" Advances in Carbohydrate Chemistry and Biochemistry; 2009; pp. 161-250; vol. 62.
Lindhorst; Essentials of Carbohydrate Chemistry and Biochemistry; 2007; pp. 157-208.
Takata et al.; "Prodrugs of Vitamin E. 1. Preparation and Enzymatic Hydrolysis of Aminoalkanecarboxylic Acid Esters of d-a-Tocopherol;" Journal of Pharmaceutical Sciences; Jan. 1995; pp. 96-100; vol. 84, No. 1.
Amylin Pharmaceuticals, Inc. and Eli Lilly and Company, "BYETTA® Approved for Use with Insulin Glargine in the U.S." Lilly News, Oct. 19, 2011, 3 pages.
"Highlights of Prescribing Information and Full Prescribing Information for LANTUS," © 2009 sanofi-aventis U.S. LLC. Revised Jun. 2009, 24 pages.
A. Magnani et al., "Novel Polysaccharide Hydrogels: Characterization and Properties." Polymers for Advanced Technologies, vol. 11, 2000, p. 488-495.
M. I. Papisov et al, "Semisynthetic Hydrophilic Polyals." Biomacromolecules, vol. 6, 2005, p. 2659-2670.
A. Yurkovetskiy et al., "Fully Degradable Hydrophilic Polyals for Protein Modification." Biomacromolecules, 2005, vol. 6, p. 2648-2658.
A. V. Yurkovetskiy et al., "Synthesis of a Macromolecular Camptothecin Conjugate with Dual Phase Drug Release." Molecular Pharmaceutics, 2004, vol. 1 No. 5, p. 375-382.
M. I. Papisov, "Acyclic Polyacetals from Polysaccharides: Biomimetic Biomedical "Stealth" Polymers." Biopolymers from Polysaccharides and Agroproteins, 2001, Chapter 19, p. 301-314.
M. Baudys et al, "Extending Insulin Action in Vivo by Conjugation to Carboxymethyl Dextran." Bioconjugate Chem, vol. 9, 1998, p. 176-183.
M. F. Ishak and Painter, T., "Kinetic Evidence for Hemiacetal Formation During the Oxidation of Dextran in Aqueous Periodate." Carbohydrate Research, vol. 64, 1978, p. 189-197.
U.S. Appl. No. 13/571,026, filed Aug. 9, 2012.
U.S. Appl. No. 14/179,212, filed Feb. 12, 2014.
U.S. Appl. No. 14/179,042, filed Feb. 12, 2014.
May 9, 2013 Office Action issued in U.S. Appl. No. 13/571,026.
Nov. 21, 2013 Office Action issued in U.S. Appl. No. 13/571,026.
"Improved Outcomes for Patients Treated with Lantus® and Apidra® Regimen Compared with Sliding Scale Insulin;" Sanofi-Aventis Press Release; Jun. 25, 2010; Paris, France.
Jul. 8, 2015 Office Action issued in U.S. Appl. No. 14/179,042.
ICI Americas Inc., "The HLB System, a time-saving guide to emulsifier selection," 1980, pp. 1-22.
Package insert for Neut® Sodium Bicarbonate Additive Solution, Publication EN-0545, Hospira Corporation, revised Nov. 2004, pp. 1-4.
Apr. 20, 2015 Office Action issued in U.S. Appl. No. 14/179,212.

* cited by examiner

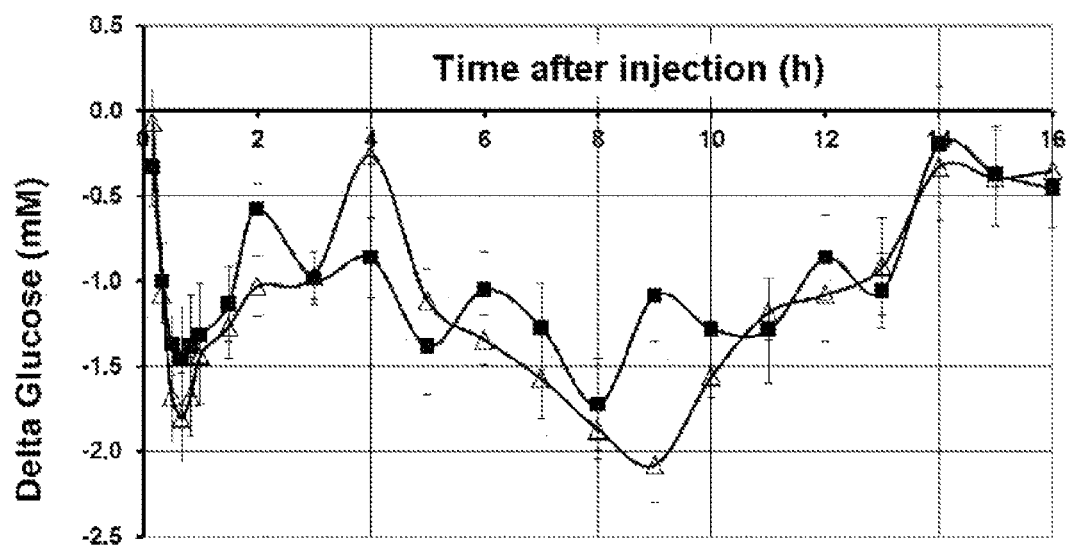

INJECTABLE SOLUTION AT PH 7 COMPRISING AT LEAST ONE BASAL INSULIN THE PI OF WHICH IS BETWEEN 5.8 AND 8.5 AND A SUBSTITUTED CO-POLYAMINO ACID

The invention relates to therapies by injection of insulin(s) for treating diabetes.

Insulin therapy, or therapy for diabetes by injection of insulin, has experienced remarkable progress over the past few years by virtue in particular of the development of new insulins which offer better correction of blood glucose level in patients in comparison with human insulin and which make it possible to simulate more closely the physiological activity of the pancreas.

When type II diabetes is diagnosed in a patient, a gradual treatment is put in place. The patient firstly takes oral antidiabetics (OADs) such as Metformin. When OADs alone are no longer sufficient to regulate the glucose level in the blood, a change in the treatment must be made and, depending on the patients' specificities, various treatment combinations can be put in place. The patient can, for example, have a treatment based on a basal insulin of glargine or detemir type as a supplement to the OADs, then subsequently, depending on the progression of the disease, a treatment based on basal insulin and prandial insulin.

Moreover, today, in order to ensure the transition from treatments with OADs, when the latter are no longer able to control the glucose level in the blood, to a basal insulin/prandial insulin treatment, the injection of GLP-1 analogs is recommended.

GLPs-1, for Glucagon-Like Peptides-1, are insulinotropic peptides or incretins, and belong to the family of gut hormones which stimulate insulin secretion when the blood glucose level is too high, for example after a meal.

Gut hormones are also called satiety hormones. They comprise in particular GLP-1 (Glucagon-like peptide-1) and GIP (Glucose-dependent insulinotropic peptide), oxyntomodulin (a proglucagon derivative), peptide YY, amylin, cholecystokinin, pancreatic polypeptide (PP), ghrelin and enterostatin which have peptide or protein structures. They also stimulate insulin secretion, in response to glucose and to fatty acids, and are therefore in this respect potential candidates for the treatment of diabetes.

Among these gut hormones, GLPs-1 are those which have to date provided the best results in the development of medicaments. They have enabled patients suffering from type II diabetes to lose weight while at the same time having a better control of their blood glucose level.

GLP-1 analogs or derivatives have thus been developed, in particular to improve their stability.

Furthermore, to cover his daily insulin needs, a diabetic patient currently has, schematically, two types of insulins that have complementary actions: prandial insulins (or "fast-acting" insulins) and basal insulins (or "slow-acting" insulins).

The prandial insulins allow a rapid management (metabolization and/or storage) of the glucose taken in during meals and snacks. The patient must inject himself with a prandial insulin before each food intake, i.e. approximately 2 to 3 injections per day. The prandial insulins most widely used are: recombinant human insulin, NovoLog® (insulin aspart from NOVO NORDISK), Humalog® (Insulin lispro from ELI LILLY) and Apidra® (insulin glulisine from SANOFI-AVENTIS).

The basal insulins maintain the glycemic homeostasis of the patient, outside periods of food intake. They act essentially to block the endogenous production of glucose (hepatic glucose). The daily dose of basal insulin generally corresponds to 40-50% of the total daily insulin needs. Depending on the basal insulin used, this dose is dispensed in 1 or 2 injections, spread out regularly over the course of the day. The basal insulins most widely used are Levemir® (insulin detemir from NOVO NORDISK) and Lantus® (insulin glargine from SANOFI-AVENTIS).

It will be noted, in the interests of being thorough, that NPH (NPH insulin for Neutral Protamine Hagedorn; Humuline NPH®, Insulatard®) is the oldest basal insulin. This formulation is the result of a precipitation of human insulin (anionic at neutral pH) using a cationic protein, protamine. The resulting microcrystals are dispersed in an aqueous suspension and dissolve slowly after subcutaneous injection. This slow dissolution provides a prolonged release of the insulin. However, this release does not provide a constant concentration of insulin over time. The release profile is bell-shaped and only lasts between 12 and 16 hours. It is therefore injected twice a day. This NPH basal insulin is much less effective than the modern basal insulins, Levemir® and Lantus®. NPH is an intermediate-action basal insulin.

The principle of NPH has evolved with the appearance of the fast-acting insulin analogs to give products called "Premix" that offer both a fast action and an interediate action. NovoLog Mix® (NOVO NORDISK) and Humalog Mix® (ELI LILLY) are formulations comprising a fast-acting insulin analog, Novolog® and Humalog®, partially complexed with protamine. These formulations thus contain insulin analog microcrystals, the action of which is termed intermediate, and an insulin component that has remained soluble, the action of which is fast. These formulations clearly offer the advantage of a fast-acting insulin, but they also have the defect of NPH, i.e. a limited duration of action of between 12 and 16 hours and an insulin with a "bell-shaped" release profile. However, these products allow patients to give themselves, in one go, an injection of an intermediate-action basal insulin with a fast-acting prandial insulin. As it happens, there are many patients who are anxious to reduce their number of injections.

The basal insulins currently marketed and currently in clinical development can be classified according to the technical solution which makes it possible to obtain the prolonged action, and, to date, two approaches are used.

The first approach, which is that of insulin detemir, is binding to albumin in vivo. Insulin detemir is an analog, which is soluble at pH 7, and which comprises a fatty acid (tetradecanoyl) side chain attached at position B29 which, in vivo, enables this insulin to associate with albumin. Its prolonged action is mainly due to this affinity for albumin after subcutaneous injection.

However, its pharmacokinetic profile does not make it possible to cover a day, which means that it is most commonly used as two injections per day.

Other basal insulins which are soluble at pH 7, such as Degludec®, are currently in development. Degludec® also comprises a fatty acid side chain attached to the insulin (hexadecandioyl-γ-L-Glu).

The second approach, which is that of insulin glargine, is precipitation at physiological pH. Insulin glargine is a human insulin analog obtained by elongation of the C-terminal part of the B chain of human insulin with two arginine residues, and by substitution of asparagine residue A21 with a glycine residue (U.S. Pat. No. 5,656,722). The addition of two arginine residues was considered in order to adjust the pI (isoelectric point) of insulin glargine to physiological pH, and thus render this human insulin analog insoluble in physiological medium.

Also, the substitution of A21 was considered in order to render insulin glargine stable at acid pH and thus to be able to formulate it in the form of an injectable solution at acid pH. During subcutaneous injection, the passing of insulin glargine from an acid pH (pH 4-4.5) to a physiological pH (neutral pH) causes it to precipitate under the skin. The slow redissolution of the insulin glargine microparticles provides a slow and prolonged action.

The hypoglycemic effect of insulin glargine is virtually constant over a period of 24 hours, which enables most patients to limit themselves to a single injection per day.

Insulin glargine is today considered to be the best basal insulin on the market.

However, the necessarily acid pH of the formulations of basal insulins, the isoelectric point of which is between 5.8 and 8.5, of insulin glargine type, can be a real drawback since this acid pH of the insulin glargine formulation sometimes causes pain at the injection in patients and especially prevents any formulation with other proteins and in particular with prandial insulins, since the latter are not stable at acid pH. The impossibility of formulating a prandial insulin at acid pH comes from the fact that a prandial insulin undergoes, under these conditions, a side reaction consisting of deamidation in position A21, which does not make it possible to meet the requirement of the US Pharmacopeia, namely less than 5% of by-products after 4 weeks at 30° C.

Thus, no one has to date sought to solubilize these basal insulins, of insulin glargine type, the isoelectric point of which is between 5.8 and 8.5, at neutral pH while at the same time maintaining a difference in solubility between the in vitro medium (the container) and the in vivo medium (under the skin), independently of the pH.

From the analysis of the compositions described in the literature and the patents, it appears that the insolubility at pH 7 of the basal insulins, of the insulin glargine type, is a prerequisite for having a slow action.

Indeed, the principle of how basal insulins of insulin glargine type, the isoelectric point of which is between 5.8 and 8.5, function is that they are soluble at acid pH and precipitate at physiological pH. This diverts those skilled in the art from any solution in which the insulin of insulin glargine type would be solubilized at pH 6-8 while keeping its essential property which is that of precipitating in subcutaneous medium.

Furthermore, this acid pH of the formulations of basal insulins, the isoelectric point of which is between 5.8 and 8.5, of insulin glargine type, even prevents any extemporaneous combination with prandial insulins at neutral pH.

Indeed, a recent clinical study, presented at the 69th Scientific Sessions of the American Diabetes Association, New Orleans, La., Jun. 5-9, 2009, made it possible to verify this limitation of the use of insulin glargine. A dose of insulin glargine and a dose of prandial insulin (in the case in point, insulin lispro) were mixed just before injection (E. Cengiz et al., 2010; Diabetes care—33(5): 1009-12). This experiment made it possible to demonstrate a significant delay in the pharmacokinetic and pharmacodynamic profiles of the prandial insulin, possibly giving rise to postprandial hyperglycemia and to nocturnal hypoglycemia. This study clearly confirms the incompatibility of insulin glargine with the fast-acting insulins currently on the market.

Moreover, the instruction leaflet for Lantus®, the commercial product based on insulin glargine from the company SANOFI-AVENTIS, explicitly informs users not to mix with a solution of prandial insulin, whatever it may be, owing to the serious risk of modifying the pharmacokinetics and the pharmacodynamics of the insulin glargine and/or of the prandial insulin mixed together.

However, from a therapeutic point of view, it has been demonstrated, as illustrated hereinafter, that treatments combining either an insulin glargine and a prandial insulin, or an insulin glargine and a GLP-1 analog, are of real interest.

As regards the combination of an insulin glargine and a prandial insulin, clinical studies made public during the 70th annual scientific sessions of the American Diabetes Association (ADA) of 2010, abstract 2163-PO and abstract number 0001-LB, in particular those carried out by the company SANOFI-AVENTIS, showed that treatments which combine Lantus®, insulin glargine and a prandial insulin are much more effective than treatments based on products of the "Premix" type, Novolog Mix® or Humalog Mix®.

As regards the combination of an insulin glargine and a GLP-1 analog, the FDA (Food and Drug Administration) approved, in October 2011, the injection of exenatide (Byetta®, AMYLIN PHARMACEUTICALS, Inc. and ELI LILLY and Company) as therapy supplementing insulin glargine for patients suffering from type II diabetes who are not able to achieve control of their blood glucose level with the basal insulin analog alone.

It so happens, owing to the fact that the very principle, set out above, of basal insulins, the isoelectric point of which is between 5.8 and 8.5, is that they are soluble at acid pH and precipitate at physiological pH, all the solutions proposed for combining them with other products, such as prandial insulins or GLP-1 analogs or derivatives, are based on tests for solubilization of the prandial insulins or GLP-1 analogs or derivatives at acid pH, see for example WO2007/121256, WO2009/021955, WO2011/144673, WO2011/147980 or else WO2009/063072.

For example, as regards the combinations of insulin glargine and fast-acting insulin, the company BIODEL has described, in particular in patent application U.S. Pat. No. 7,718,609, compositions comprising a basal insulin and a prandial insulin at a pH of between 3.0 and 4.2 in the presence of a chelating agent and of polyacids. This patent teaches how to make compatible a prandial insulin at acid pH in the presence of insulin glargine. It does not teach how to prepare a combination of insulin of insulin glargine type and of a prandial insulin at neutral pH.

Likewise by way of example, as regards the solubilization of insulin glargine at neutral pH and the combinations with a GLP-1 analog, mention will be made of patent application WO2011/144676 published on Nov. 24, 2011, in the name of SANOFI-AVENTIS, which describes formulations, at pH 9.5, of glargine with the cyclodextrin SVE4-β-CYD in which the solubility of glargine is improved from 0.75 mM to 1.25 mM. This application also mentions compositions additionally comprising a GLP-1, although they are not exemplified. The solubilizing effect at pH 7.4 in a phosphate buffer is mentioned. These results of solubilization at pH 7.4 are described in the publication entitled "Effect of sulfobutyl ether-β-cyclodextrin on bioavailability of insulin glargine and blood glucose level after subcutaneous injection to rats" (*International Journal of Pharmaceutics,* 419 (2011), 71-76) in FIG. 3A. The sulfobutyl ether-β-cyclodextrin improves the solubility of the insulin glargine at pH 7.4 from 5 μM to 8 μM, which is of no therapeutic interest, since the commercial concentration of insulin glargine is 600 μM (100 IU/ml). The problem has thus not been satisfactorily solved by the invention described in this patent application.

To our knowledge, a formulation which is stable at physiological pH, comprising a basal insulin, the isoelectric point of which is between 5.8 and 8.5, alone or in combination with a prandial insulin and/or a gut hormone, in which the solubility of the insulin is sufficient for a therapeutic treatment, has therefore never been described.

The present invention, by solving this problem of solubility at a pH between 6.6 and 7.8, makes it possible:

- to propose an injectable composition, intended for the treatment of diabetes, comprising a basal insulin, the isoelectric point of which is between 5.8 and 8.5, in the form of a homogeneous solution at a pH of between 6.6 and 7.8, while at the same time retaining its biological activity and its action profile;
- to propose an injectable composition in the form of a homogeneous solution at a pH of between 6.6 and 7.8, also comprising a combination of a basal insulin, the isoelectric point of which is between 5.8 and 8.5, and of a prandial insulin without modification of the activity profile of the prandial insulin which is soluble at pH 6-8 and unstable at acid pH, while at the same time maintaining the slow action profile specific to the basal insulin;
- to propose an injectable composition in the form of a homogeneous solution at a pH of between 6.6 and 7.8, also comprising a combination of a basal insulin, the isoelectric point of which is between 5.8 and 8.5, and of a gut hormone derivative or analog, such as GLP-1 or glucagon-like peptide-1,
- to reduce the number of injections in the context of the treatment of diabetes,
- for said compositions to comply with the requirements of the US and European Pharmacopeias.

Surprisingly, the compositions according to the invention make it possible to solubilize at a pH of between 6.6 and 7.8 a basal insulin, the isoelectric point of which is between 5.8 and 8.5.

Surprisingly, the compositions according to the invention make it possible to maintain the duration of the hypoglycemic activity of the basal insulin, the isoelectric point of which is between 5.8 and 8.5, despite its solubilization at a pH of between 6.6 and 7.8 before injection. This notable property comes from the fact that the insulin of insulin glargine type solubilized at a pH of between 6.6 and 7.8 in the composition of the invention precipitates in subcutaneous medium through a change in composition of the medium. The element which triggers the precipitation of the insulin of insulin glargine type is no longer the pH modification, but a modification of the composition of the environment when the pharmaceutical composition passes from the container to the physiological medium. Surprisingly, in the combinations of insulin of insulin glargine type with a prandial insulin, which are subjects of the invention, the fast action of the prandial insulin is preserved despite the precipitation of the insulin of glargine type in subcutaneous medium.

The solution according to the invention which makes it possible to solubilize the basal insulin, the isoelectric point of which is between 5.6 and 3.5, at a pH of between 6.6 and 7.8 preserves its biological activity.

In the combinations of the insulin of insulin glargine type with a prandial insulin, which are subjects of the invention, the fast action of the prandial insulin is preserved despite the precipitation of the insulin of insulin glargine type in subcutaneous medium. Furthermore, the presence of the prandial insulin does not modify the solubility of the basal insulin at a pH of between 6.6 and 7.8 and likewise does not modify the precipitation properties of the basal insulin.

The invention relates to a composition in the form of an injectable aqueous solution, the pH of which is between 6.6 and 7.8, comprising at least:

a) a basal insulin, the isoelectric point pI of which is between 5.8 and 8.5;
b) a co-polyamino acid bearing carboxylate charges and substituted with hydrophobic groups, chosen from the co-polyamino acids of formula I:

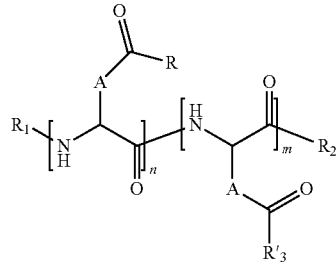

formula I in which:
A independently represents either a —CH$_2$— group (aspartic unit) or a —CH$_2$—CH$_2$— group (glutamic unit),
$R_1$ is a radical chosen from the group consisting of an H, a linear C$_2$ to C$_{10}$ acyl group, a branched C$_3$ to C$_{10}$ acyl group, a benzyl, a terminal "amino acid" unit and a pyroglutamate,
$R_2$ is an —NR'R" radical, R' and R" which may be identical or different, being chosen from the group consisting of H, linear or branched or cyclic C$_2$ to C$_{30}$ alkyls and benzyl, and said R' and R" alkyls being alkyls which can together form one or more saturated, unsaturated and/or aromatic rings which are carbon-based and/or which can comprise heteroatoms, chosen from the group consisting of O, N and S.
$R'_3$ is a radical chosen from the group consisting of the radicals of formulae —OR$_3$, II or II':

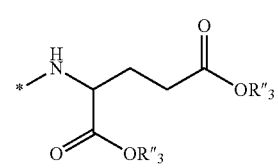

formula II

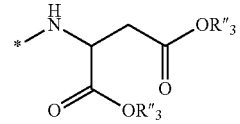

formula II' in which * indicates the site of attachment of the co-polyamino acid
$R_3$ and R"$_3$, which may be identical or different, represent an H or a cationic entity chosen from the group comprising metal cations,
—R is a radical chosen from the group consisting of a saturated or unsaturated, linear or branched C$_8$ to C$_{30}$ radical which can comprise heteroatoms or a C$_8$ to C$_{30}$ radical which can form rings which are carbon-based or which can comprise heteroatoms, which are saturated, unsaturated and/or aromatic, said rings possibly being ortho-condensed or ped-condensed, or a radical of formula III or III' as defined below:

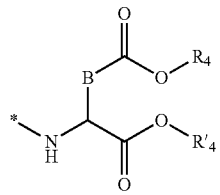

formula III

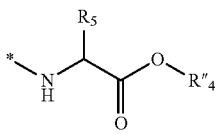

formula III' in which * indicates the site of attachment to the co-polyamino acid, and $R_4$, and $R'_4$, which may be identical or different, represent an H, a cationic entity chosen from the group comprising metal cations, an $R''_4$ radical or an $R'''_4$ radical, and at least one of $R_4$ and $R'_4$ is equal to $R''_4$, $R''_4$ represents a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, $R'''_4$ represents a saturated or unsaturated, linear or branched $C_1$ to $C_7$ radical which can comprise heteroatoms or a $C_1$ to $C_7$ radical which can form rings which are carbon-based or which can comprise heteroatoms, which are saturated, unsaturated and/or aromatic, said rings possibly being ortho-condensed or peri-condensed, and B independently represents either a —$CH_1$— group (aspartic unit) or a —$CH_2CH_2$— group (glutamic unit), $R_5$ is a radical chosen from the group consisting of an H, a linear or branched $C_1$ to $C_4$ alkyl or a benzyl group, n/(n+m) is defined as the molar degree of grafting with hydrophobic radical of the monomeric units and is between 1 and 50 mol %, n+m represents the degree of polymerization of the co-polyamino acid, i.e. the average number of monomeric units per chain of co-polyamino acid, and $5 \leq n+m \leq 1000$.

The co-polyamino acid is a random co-polyamino acid.

The $R'_3$, $R_3$, $R''_3$, R, $R_4$, $R'_4$, $R''_4$, $R'''_4$, R', R" and $R_5$ radicals and the groups A and B are each independently identical or different from one monomeric unit to another.

In one embodiment, the composition according to the invention is characterized in that the co-polyamino acids of formula I can also comprise monomeric units of formula VI and/or VI':

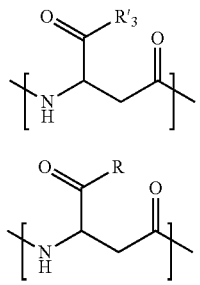

formula VI

formula VI'

In one embodiment, the co-polyamino acid bearing carboxylate charges and substituted with hydrophobic groups is chosen from the co-polyamino acids of formula IV:

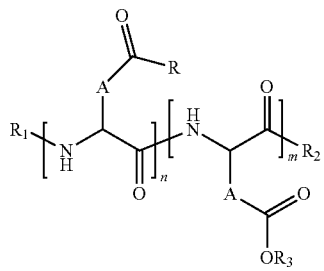

formula IV in which:
the radicals or groups A, $R_1$, $R_2$, R and $R_3$ are defined as in formula I.

The co-polyamino acid is a random co-polyamino acid.

The $R'_3$, $R_3$, $R''_3$, R, $R_4$, $R'_4$, $R''_4$, $R'''_4$, R', R" and $R_5$ radicals and the groups A and B are each independently identical or different from one monomeric unit to another.

In one embodiment, the co-polyamino acid bearing carboxylate charges and substituted with hydrophobic groups is chosen from the co-polyamino acids of formula IV:

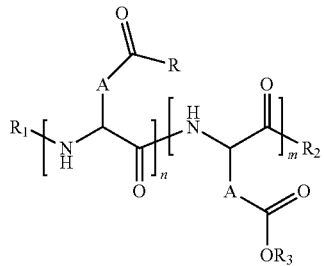

formula IV in which:
A independently represents a —$CH_2$— group (aspartic unit) or a —$CH_2$—$CH_2$— group (glutamic unit), $R_1$ is chosen from the group consisting of an H, a linear to $C_2$ to $C_{10}$ acyl group, a branched $C_3$ to $C_{10}$ acyl group, a benzyl, a terminal "amino acid" unit and a pyroglutamate, $R_2$ is an —NR'R" radical, R' and R", which may be identical or different, being chosen from the group consisting of H, linear or branched or cyclic $C_2$ to $C_{10}$ alkyls and benzyl, and said R' and R" alkyls being alkyls which can together form saturated, unsaturated and/or aromatic rings which are carbon-based and/or which can comprise heteroatoms, chosen from the group consisting of O, N and S, the $R_3$ groups, which may be identical or different, are chosen from the group consisting of an H or a cationic entity chosen from the group comprising metal cations, the R groups each represent, independently from one another, a radical chosen from the radicals of general formula V or V':

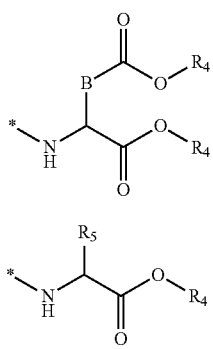

formula V formula V' in which * indicates the site of attachment to the co-polyamino acid, and $R_4$ a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, B independently represents a —$CH_2$— group (aspartic unit) or a —$CH_2$—$CH_2$— group (glutamic unit), $R_5$ independently represents an H, a linear or branched $C_1$ to $C_4$ alkyl or a benzyl group, or R is a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, n/(n+m) is defined as the molar degree of grafting with hydrophobic radical of the monomeric units, and is between 1 and 50 mol %, n+m represents the degree of polymerization of the co-polyamino acid, i.e. the average number of monomeric units per chain of co-polyamino acid, and $5 \leq n+m \leq 1000$.

The co-polyamino acid is a random co-polyamino acid.

The $R'_3$, $R_3$, $R''_3$, R, $R_4$, $R'_4$, $R''_4$, $R'''_4$, R', R'' and $R_5$ radicals and the groups A and B are each independently identical or different from one monomeric unit to another.

In one embodiment, the co-polyamino add bearing carboxylate charges and substituted with hydrophobic groups is chosen from the co-polyamino acids of formula IV:

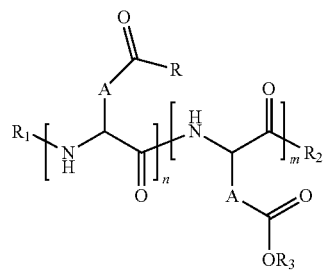

formula IV in which:

A independently represents a —$CH_2$— group (aspartic unit) or a —$CH_2$—$CH_2$— group (glutamic unit), $R_1$ is chosen from the group consisting of an H, a linear $C_2$ to $C_{10}$ acyl group, a branched $C_3$ to $C_{10}$ acyl group, a benzyl, a terminal "amino acid" unit and a pyroglutamate, $R_2$ is chosen from the group consisting of:

a secondary amino radical —NR'R", R' and R", which may be identical or different, being chosen from the group consisting of linear or branched or cyclic $C_2$ to $C_{10}$ alkyls and benzyl, and said R' and R" alkyls being alkyls which can together form saturated, unsaturated and/or aromatic rings which are carbon-based and/or which can comprise heteroatoms, chosen from the group consisting of O, N and S, the $R_3$ groups, which may be identical or different, are chosen from the group consisting of an H or a cationic entity chosen from the group comprising metal cations, the R groups each represent, independently from one another, a radical chosen from the radicals of general formula V or V':

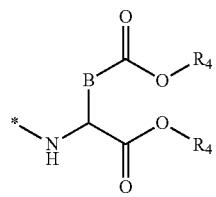

formula V

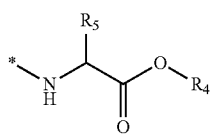

formula V' in which * indicates the site of attachment to the co-polyamino acid, and $R_4$ represents a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, B independently represents a —$CH_2$— group (aspartic unit) or a —$CH_2$—$CH_2$— group (glutamic unit), $R_5$ independently represents an H, a linear or branched $C_1$ to $C_4$ alkyl or a benzyl group, or R is a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, n/(n+m) is defined as the molar degree of grafting with hydrophobic radical of the monomeric units and is between 1 and 50 mol %, n+m represents the degree of polymerization of the co-polyamino acid, i.e. the average number of monomeric units per chain of co-polyamino acid, and $5 \le n+m \le 1000$.

The $R'_3$, $R_3$, $R''_3$, R, $R_4$, $R'_4$, $R''_4$, $R'''_4$, R', R" and $R_5$ radicals and the groups A and B are each independently identical or different from one monomeric unit to another.

In one embodiment, the co-polyamino acid bearing carboxylate charges and substituted with hydrophobic groups is chosen from the co-polyamino acids of formula IV:

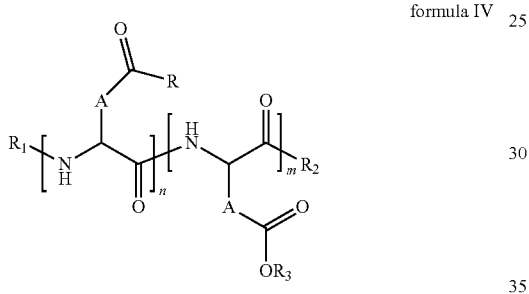

formula IV in which:
- A independently represents a —$CH_2$— group (aspartic unit) or a —$CH_2$—$CH_2$— group (glutamic unit),
- $R_1$ is chosen from the group consisting of an H, a linear $C_2$ to $C_{10}$ acyl group, a branched $C_3$ to $C_{10}$ acyl group, a benzy, a terminal "amino acid" unit and a pyroglutamate,
- $R_2$ represents an —$NHR_{11}$ radical in which $R_{11}$ is chosen from the group consisting of an H, a linear $C_2$ to $C_{10}$ or branched $C_3$ to $C_{10}$ alkyl, or a benzyl or a $C_2$ to $C_{30}$ acyl which is linear or branched and which can comprise heteroatoms chosen from the group consisting of N, O and S,
- the $R_3$ groups, which may be identical or different, are chosen from the group consisting of an H or a cationic entity chosen from the group comprising metal cations,
- the R groups each represent, independently from one another, a radical chosen from the radicals of general formula V or V':

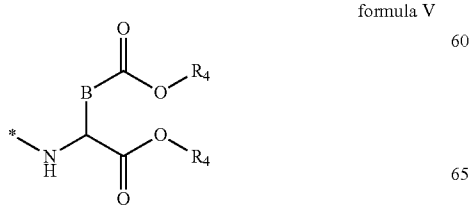

formula V

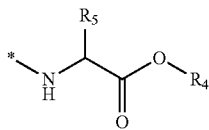

formula V' in which * indicates the site of attachment to the co-polyamino acid, and $R_4$ represents a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, B independently represents a —$CH_2$— group (aspartic unit) or a —$CH_2$—$CH_2$— group (glutamic unit), $R_5$ independently represents an H, a linear or branched $C_1$ to $C_4$ alkyl or a benzyl group, or R is a saturated or unsaturated, linear or branched $C_8$ to $C_{30}$ radical which can comprise heteroatoms or a $C_8$ to $C_{30}$ radical which can form rings which are carbon-based or which can comprise heteroatoms, which are saturated, unsaturated and/or aromatic, said rings possibly being ortho-condensed or peri-condensed, n/(n+m) is defined as the molar degree of grafting with hydrophobic radical of the monomeric units and is between 1 and 50 mol %, n+m represents the degree of polymerization of the co-polyamino acid, i.e. the average number of monomeric units per chain of co-polyamino acid, and $5 \le n+m \le 1000$.

In one embodiment, the composition according to the invention is characterized in that the co-polyamino acid is chosen from the co-polyamino acids of formula I or IV, in which the group A is a —$CH_2$— group (aspartic unit).

When the co-polyamino acid consists of aspartic units, they can undergo structural rearrangements.

In one embodiment, the composition according to the invention is characterized in that the co-polyamino acids of formula I or IV can also comprise monomeric units of formula VI" and/or VI':

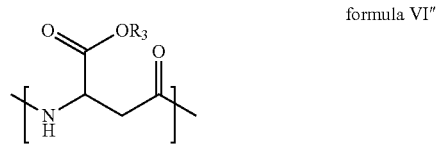

formula VI"

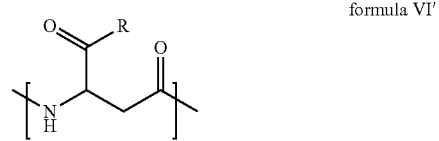

formula VI'

In one embodiment, the composition according to the invention is characterized in that the co-polyamino acid is chosen from the co-polyamino acids of formula I or IV, in which the group A is a —$CH_2$—$CH_2$— group (glutamic unit).

In one embodiment, the composition according to the invention is characterized in that the co-polyamino acid is chosen from the co-polyamino acids of formula I or IV, in which R is chosen from the group of radicals derived from hydrophobic alcohols.

The R radical derived from a hydrophobic alcohol is obtained by reaction of an alcohol function of the hydrophobic alcohol and a carboxylic acid function of the co-polyamino acid.

In one embodiment, the radical derived from hydrophobic alcohols is chosen from the radicals derived from alcohols consisting of an unsaturated or saturated alkyl chain comprising from 8 to 18 carbons.

In one embodiment, the radical derived from hydrophobic alcohols is chosen from the group consisting of the radicals derived from myristyl alcohol, cetyl alcohol, stearyl alcohol or oleyl alcohol.

In one embodiment, the radical derived from hydrophobic alcohols is a radical derived from cholesterol derivatives.

In one embodiment, the radical derived from hydrophobic alcohols is chosen from the radicals derived from tocopherol alcohols.

In one embodiment, the radical derived from hydrophobic alcohols is chosen from the radicals derived from alcohols bearing an aryl group.

In one embodiment, the radical derived from hydrophobic alcohols is chosen from the radicals derived from benzyl alcohol or phenylethyl alcohol.

In one embodiment, the radical derived from hydrophobic alcohols is chosen from the co-polyamino acids of formula I, in which R is a radical derived from lauryl alcohol.

In one embodiment, the radical derived from hydrophobic alcohols is a radical derived from tocopherol.

In one embodiment, the radical derived from hydrophobic alcohols is a radical derived from cholesterol.

In one embodiment, the composition according to the invention is characterized in that the co-polyamino acid is chosen from the co-polyamino adds of formula I or IV, in which the group R is a radical of -L-R''' type, the R''' radical being derived from a hydrophobic acid and the L radical being a linker arm comprising from 2 to 10 carbons, which is linear or branched or which can comprise heteroatoms chosen from the group consisting of N, O and S, derived from a diol, from a diamine or from an amino alcohol.

The radical derived from a hydrophobic acid is derived from the reaction of the acid function of the hydrophobic acid and of an alcohol or amine function of the diamine, of the diol or of the amino alcohol.

The radical L is derived, on the one hand, from the reaction of the acid function of the hydrophobic acid and of an alcohol or amine function of the diamine, of the diol or of the amino alcohol and, on the other hand, from the reaction between a carboxylic acid function of the co-polyamino acid and an alcohol or amine function of the diamine, of the diol or of the amino alcohol.

In one embodiment, the hydrophobic acids are chosen from the group consisting of fatty acids.

In one embodiment, the fatty acids are chosen from the group consisting of linear fatty acids.

In one embodiment, the linear fatty acids are chosen from the group consisting of caproic acid, enanthic acid, caprylic acid, capric acid, nonanoic acid, decanoic acid, undecanoic acid, dodecanoic acid, palmitic acid, stearic acid, arachidic acid, behenic acid, tricosanoic acid, lignoceric acid, heptacosanoic acid and octacosanoic acid.

In one embodiment, the fatty acids are chosen from the group consisting of unsaturated fatty acids.

In one embodiment, the unsaturated fatty acids are chosen from the group consisting of myristoleic acid, palmitoleic acid, oleic acid, elaidic acid, linoleic acid, alpha-linoleic acid, arachidonic add, eicosapentaenoic acid, erucic acid and docosahexaenoic acid.

In one embodiment, the fatty acids are chosen from the group consisting of bile acids and derivatives thereof.

In one embodiment, the bile acids and derivatives thereof are chosen from the group consisting of cholic acid, dehydrocholic acid, deoxycholic acid and chenodeoxycholic acid.

In one embodiment, the diamines are chosen from the group consisting of ethylenediamine and lysine and its derivatives.

In one embodiment, the diamines are chosen from the group consisting of diethylene glycol diamine and triethylene glycol diamine.

In one embodiment, the dials are chosen from the group consisting of glycerol, diglycerol and triglycerol.

In one embodiment, the dialcohols are chosen from the group consisting of diethylene glycol and triethylene glycol.

In one embodiment, the amino alcohols are chosen from the group consisting of ethanolamine, 2-aminopropanol, isopropanolamine, 3-amino-1,2-propanediol, diethanolamine, diisopropanolamine, tromethamine (Tris) and 2-(2-aminoethoxy)ethanol.

In one embodiment, the alcohol amines are chosen from the group consisting of reduced amino acids.

In one embodiment, the reduced amino acids are chosen from the group consisting of alaninol, valinol, leucinal, isoleucinol, prolinol, phenylalaninol, serinol and threoninol.

In one embodiment, the alcohol amines are chosen from the group consisting of charged amino acids.

In one embodiment, the charged amino acids are chosen from the group consisting of serine and threonine.

In one embodiment, L is a trivalent radical.

In one embodiment, L is a trivalent radical chosen from the group consisting of triamines, dialcohol amines, diamine alcohols and diamine acids.

In one embodiment, the composition according to the invention is characterized in that the co-polyamino acid is chosen from the co-polyamino acids of formula I or IV, in which $R_2$ is —N-morpholyl.

In one embodiment, the composition according to the invention is characterized in that the co-polyamino acid is chosen from the co-polyamino acids of formula I, in which the $R_2$ group is a radical derived from an amino acid and is chosen from the radicals of formula VII:

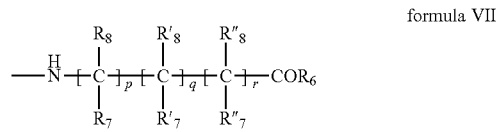

formula VII in which:

$R_6$ is —OH, —OR, or —$NHR_{10}$ and $R_7$, $R'_7$, $R''_7$, $R_8$, $R'_8$, $R''_8$, $R_9$ and $R_{10}$, which may be identical or different, independently represent an H, a linear $C_2$ to $C_{10}$ alkyl, a branched $C_3$ to $C_{10}$ alkyl or a benzyl, with $0 \le p \le 3$, $0 \le q \le 3$, $0 \le r \le 3$ and $1 \le p+q+r \le 10$.

In one embodiment, the composition according to the invention is characterized in that the co-polyamino acid is chosen from the co-polyamino acids of formula I or IV, in which $R_4$, $R'_4$ and/or $R''_4$, which may be identical or different, are chosen from the group of radicals derived from hydrophobic alcohols.

The radicals derived from hydrophobic alcohols are as defined above, and are obtained by reaction of an acid function borne by a precursor of a radical of formula III, III', V or V', and the alcohol function of the hydrophobic alcohol.

In one embodiment, the radical derived from hydrophobic alcohols is chosen from the radicals derived from alcohols consisting of an unsaturated or saturated alkyl chain comprising from 8 to 18 carbons.

In one embodiment, the radical derived from hydrophobic alcohols is chosen from the group consisting of the radicals derived from myristyl alcohol, cetyl alcohol, stearyl alcohol or oleyl alcohol.

In one embodiment, the radical derived from hydrophobic alcohols is a radical derived from cholesterol derivatives.

In one embodiment, the radical derived from hydrophobic alcohols is chosen from the radicals derived from tocopherols.

In one embodiment, the radical derived from hydrophobic alcohols is chosen from the radicals derived from alcohols bearing an aryl group.

In one embodiment, the radical derived from hydrophobic alcohols is chosen from the radicals derived from benzyl alcohol or phenethyl alcohol.

In one embodiment, the radical derived from hydrophobic alcohols is chosen from the co-polyamino acids of formula I or IV, in which R is a radical derived from lauryl alcohol.

In one embodiment, the radical derived from hydrophobic alcohols is a radical derived from cholesterol.

In one embodiment, the radical derived from hydrophobic alcohols is a radical derived from tocopherol.

In one embodiment, the composition according to the invention is characterized in that the co-polyamino acid is chosen from the co-polyamino adds of formula I or IV, in which the $R_5$ group is an isobutyl radical.

In one embodiment, the composition according to the invention is characterized in that the co-polyamino acid is chosen from the co-polyamino acids of formula I or IV, in which the $R_5$ group is an H.

In one embodiment, the composition according to the invention is characterized in that the co-polyamino acid is chosen from the co-polyamino acids of formula I or IV, in which the $R_5$ group is chosen from the group consisting of methyl, isopropyl, sec-butyl and benzyl radicals.

In one embodiment, the composition according to the invention is characterized in that the co-polyamino acid is chosen from the co-polyamino acids of formula I or IV, in which n+m is between 5 and 500.

In one embodiment, the composition according to the invention is characterized in that the co-polyamino acid is chosen from the co-polyamino acids of formula I or IV, in which n+m is between 5 and 250.

In one embodiment, the composition according to the invention is characterized in that the co-polyamino acid is chosen from the co-polyamino acids of formula I or IV, in which n+m is between 5 and 100.

In one embodiment, the composition according to the invention is characterized in that the co-polyamino acid is chosen from the co-polyamino acids of formula I or IV, in which n+m is between 5 and 50.

In one embodiment, the composition according to the invention is characterized in that the co-polyamino acid is chosen from the co-polyamino acids of formula I or IV, in which n+m is between 5 and 25.

In one embodiment, the composition according to the invention is characterized in that the co-polyamino acid is chosen from the co-polyamino acids of formula I or IV, in which n+m is between 10 and 500.

In one embodiment, the composition according to the invention is characterized in that the co-polyamino acid is chosen from the co-polyamino acids of formula I or IV, in which n+m is between 15 and 250.

In one embodiment, the composition according to the invention is characterized in that the co-polyamino acid is chosen from the co-polyamino acids of formula I or IV, in which n/(n+m) is between 1 and 30 mol %.

In one embodiment, the composition according to the invention is characterized in that the co-polyamino acid is chosen from the co-polyamino acids of formula I or IV, in which n/(n+m) is between 1 and 20 mol %.

In one embodiment, the composition according to the invention is characterized in that the co-polyamino acid is chosen from the co-polyamino acids of formula I or IV, in which n/(n+m) is between 1 and 10 mol %.

In one embodiment, the composition according to the invention is characterized in that the co-polyamino acid is chosen from the co-polyamino acids of formula I or IV, in which n/(n+m) is between 1 and 5 mol %.

In one embodiment, the composition according to the invention is characterized in that the co-polyamino acid is derived from a polyamino acid obtained by ring-opening polymerization of a glutamic acid N-carboxyanhydride derivative or of an aspartic acid N-carboxyanhydride derivative.

In one embodiment, the composition according to the invention is characterized in that the co-polyamino acid is derived from a polyamino acid obtained by polymerization of a glutamic acid N-carboxyanhydride derivative or of an aspartic acid N-carboxyanhydride derivative as described in the review article Adv. Polym. Sci. 2006, 202, 1-18 (Derning, T. J.).

In one embodiment, the composition according to the invention is characterized in that the co-polyamino acid is derived from a polyamino acid obtained by polymerization of a glutamic acid N-carboxyanhydride derivative or of an aspartic acid N-carboxyanhydride derivative using as initiator an organometallic complex of a transition metal as described in the publication Nature 1997, 390, 386-389 (Derning, T. J.).

In one embodiment, the composition according to the invention is characterized in that the co-polyamino acid is derived from a polyamino acid obtained by polymerization of a glutamic acid N-carboxyanhydride derivative or of an aspartic acid N-carboxyanhydride derivative using as initiator aqueous ammonia or a primary amine as described in patent FR 2,601,226 (Touraud, F. et al.) and the references cited in this patent.

In one embodiment, the composition according to the invention is characterized in that the co-polyamino acid is derived from a polyamino acid obtained by polymerization of a glutamic acid N-carboxyanhydride derivative or of an aspartic acid N-carboxyanhydride derivative using as initiator hexamethyldisilazane as described in the publication J. Am. Chem. Soc. 2007, 129, 14114-14115 (Lu H. et al.) or a silylated amine as described in the publication J. Am. Chem. Soc. 2008, 130. 12562-12563 (Lu H. et al.).

In one embodiment, the composition according to the invention is characterized in that the co-polyamino acid is obtained by peptide synthesis on a support using a peptide synthesizer.

In one embodiment, the composition according to the invention is characterized in that the co-polyamino acid is obtained by liquid-phase peptide synthesis.

In one embodiment, the composition according to the invention is characterized in that the co-polyamino acid is obtained by grafting a hydrophobic group on to a poly-L-glutamic acid or poly-L-aspartic acid using the processes for forming an amide bond that are well known to those skilled in the art.

In one embodiment, the composition according to the invention is characterized in that the co-polyamino acid is obtained by grafting a hydrophobic group on to a poly-L-glutamic acid or poly-L-aspartic acid as described in patent FR 2,840,614 (Ping, C. U. et al.).

The expression "basal insulin, the isoelectric point of which is between 5.8 and 8.5" is intended to mean an insulin which is unsoluble at pH 7 and the duration of action of which is between 8 and 24 hours or more in the standard diabetes models.

These basal insulins, the isoelectric point of which is between 5.8 and 8.5, are recombinant insulins of which the primary structure has been modified mainly by introducing basic amino acids such as arginine or lysine. They are described, for example, in the following patents, patent applications or publications: WO 2003/053339, WO 2004/096854, U.S. Pat. Nos. 5,656,722 and 6,100,376, the content of which is incorporated by way of reference.

In one embodiment, the basal insulin, the isoelectric point of which is between 5.8 and 8.5, is insulin glargine.

In one embodiment, the compositions according to the invention comprise between 40 and 500 IU/ml of basal insulin, the isoelectric point of which is between 5.8 and 8.5.

In one embodiment, the compositions according to the invention comprise 40 IU/ml of basal insulin, the isoelectric point of which is between 5.8 and 8.5.

In one embodiment, the compositions according to the invention comprise 100 IU/ml (i.e. approximately 3.6 mg/ml) of basal insulin, the isoelectric point of which is between 5.8 and 8.5.

In one embodiment, the compositions according to the invention comprise 200 IU/ml of basal insulin, the isoelectric point of which is between 5.8 and 6.5.

In one embodiment, the compositions according to the invention comprise 300 IU/ml of basal insulin, the isoelectric point of which is between 5.8 and 8.5.

In one embodiment, the compositions according to the invention comprise 400 IU/ml of basal insulin, the isoelectric point of which is between 5.8 and 8.5.

In one embodiment, the compositions according to the invention comprise 500 IU/ml of basal insulin, the isoelectric point of which is between 5.8 and 8.5.

In one embodiment, the weight ratio between the basal insulin, the isoelectric point of which is between 5.8 and 6.5, and the substituted co-polyamino acid, i.e. the substituted co-polyamino acid/basal insulin, is between 0.2 and 30.

In one embodiment, the weight ratio is between 0.2 and 15.
In one embodiment, the weight ratio is between 0.2 and 10.
In one embodiment, the weight ratio is between 0.2 and 4.
In one embodiment, the weight ratio is between 0.2 and 3.
In one embodiment, the weight ratio is between 0.2 and 2.
In one embodiment, the weight ratio is between 0.2 and 1.
In one embodiment, the weight ratio is equal to 1.

In one embodiment, the concentration of substituted co-polyamino acid is at most 100 mg/ml.
In one embodiment, the concentration of substituted co-polyamino acid is at most 80 mg/ml.
In one embodiment, the concentration of substituted co-polyamino acid is at most 60 mg/ml.
In one embodiment, the concentration of substituted co-polyamino acid is at most 40 mg/ml.
In one embodiment, the concentration of substituted co-polyamino acid is at most 20 mg/ml.
In one embodiment, the concentration of substituted co-polyamino acid is at most 10 mg/ml.

In one embodiment, the compositions according to the invention also comprise a prandial insulin. The prandial insulins are soluble at pH 7.

The term "prandial insulin" is intended to mean an insulin termed fast-acting or "regular".

The prandial insulins termed fast-acting are insulins which must respond to the needs caused by the ingestion of proteins and carbohydrates during a meal; they must act in less than 30 minutes.

In one embodiment, the prandial insulin termed "regular" is human insulin.

In one embodiment, the insulin is a recombinant human insulin as described in the European Pharmacopeia and the US Pharmacopeia.

The human insulin is, for example, sold under the brands Humulin® (ELI LILLY) and Novolin® (NOVO NORDISK).

The prandial insulins termed fast-acting are insulins which are obtained by recombination and the primary structure of which has been modified so as to reduce their acting time.

In one embodiment, the prandial insulins termed fast-acting are chosen from the group comprising insulin lispro (Humalog®), insulin glulisine (Apidra®) and insulin aspart (NovoLog®).

In one embodiment, the prandial insulin is insulin lispro.
In one embodiment, the prandial insulin is insulin glulisine.
In one embodiment, the prandial insulin is insulin aspart.

In one embodiment, the compositions according to the invention comprise in total between 40 and 800 IU/ml of insulin with a combination of prandial insulin and basal insulin, the isoelectric point of which is between 5.6 and 8.5.

In one embodiment, the compositions according to the invention comprise in total between 40 and 500 IU/ml of insulin with a combination of prandial insulin and basal insulin, the isoelectric point of which is between 5.6 and 8.5.

In one embodiment, the compositions according to the invention comprise in total 800 IU/ml of insulin with a combination of prandial insulin and basal insulin, the isoelectric point of which is between 5.8 and 8.5.

In one embodiment, the compositions according to the invention comprise in total 700 of insulin with a combination of prandial insulin and basal insulin, the isoelectric point of which is between 5.8 and 8.5.

In one embodiment, the compositions according to the invention comprise in total 600 of insulin with a combination of prandial insulin and basal insulin, the isoelectric point of which is between 5.8 and 8.5.

In one embodiment, the compositions according to the invention comprise in total 500 IU/ml of insulin with a combination of prandial insulin and basal insulin, the isoelectric point of which is between 5.8 and 8.5.

In one embodiment, the compositions according to the invention comprise in total 400 IU/ml of insulin with a combination of prandial insulin and basal insulin, the isoelectric point of which is between 5.8 and 8.5.

In one embodiment, the compositions according to the invention comprise in total 300 IU/ml of insulin with a combination of prandial insulin and basal insulin, the isoelectric point of which is between 5.8 and 8.5.

In one embodiment, the compositions according to the invention comprise in total 200 IU/ml of insulin with a combination of prandial insulin and basal insulin, the isoelectric point of which is between 5.8 and 8.5.

In one embodiment, the compositions according to the invention comprise in total 100 IU/ml of insulin with a combination of prandial insulin and basal insulin, the isoelectric point of which is between 5.8 and 8.5.

In one embodiment, the compositions according to the invention comprise in total 40 IU/ml of insulin with a combination of prandial insulin and basal insulin, the isoelectric point of which is between 5.8 and 8.5.

The proportions between the basal insulin, the isoelectric point of which is between 5.8 and 8.5, and the prandial insulin are, for example, as a percentage, 25/75, 30/70, 40/60, 50/50, 60/40, 70/30, 80/20 or 90/10 for formulations as described above comprising from 40 to 800 IU/ml. However, any other proportion can be prepared.

In one embodiment, the compositions according to the invention also comprise a gut hormone.

The term "gut hormones" intended to mean hormones chosen from the group consisting of GLP-1 (Glucagon-like peptide-1) and GIP (Glucose-dependent insulinotropic peptide), oxyntomodulin (a proglucagon derivative), peptide YY, amylin, cholecystokinin, pancreatic polypeptide (PP), ghrelin and enterostatin, their analogs or derivatives and/or their pharmaceutically acceptable salts.

In one embodiment, the gut hormones are GLP-1 analogs or derivatives chosen from the group consisting of exenatide or Byetta®, developed by ELI LILLY & CO and AMYLIN PHARMACEUTICALS, liraglutide or Victoza® developed by NOVO NORDISK, or lixisenatide or Lyxumia® developed by SANOFI-AVENTIS, their analogs or derivatives and their pharmaceutically acceptable salts.

In one embodiment, the gut hormone is exenatide or Byetta®, its analogs or derivatives and their pharmaceutically acceptable salts.

In one embodiment, the gut hormone is liraglutide or Victoza®, its analogs or derivatives and their pharmaceutically acceptable salts.

In one embodiment, the gut hormone is lixisenatide or Lyxumia®, its analogs or derivatives and their pharmaceutically acceptable salts.

The term "analog", when it is used with reference to a peptide or a protein, is intended to mean a peptide or a protein in which one or more constituent amino acid residues have been substituted with other amino acid residues and/or in which one or more constituent amino add residues have been deleted and/or in which one or more constituent amino acid residues have been added. The percentage homology accepted for the present definition of an analog is 50%.

The term "derivative", when it is used with reference to a peptide or a protein, is intended to mean a peptide or a protein or an analog which has been chemically modified with a substituent which is not present in the reference peptide or protein or analog, i.e. a peptide or a protein which has been modified by creating covalent bonds, so as to introduce substituents.

In one embodiment, the substituent is chosen from the group consisting of fatty chains.

In one embodiment, the concentration of gut hormone included in a range of from 0.01 to 10 mg/ml.

In one embodiment, the concentration of exenatide, its analogs or derivatives and their pharmaceutically acceptable salts is included in a range of from 0.05 to 0.5 mg/ml.

In one embodiment, the concentration of liraglutide, its analogs or derivatives and their pharmaceutically acceptable salts is included in a range of from 1 to 10 mg/ml.

In one embodiment, the concentration of lixisenatide, its analogs or derivatives and their pharmaceutically acceptable salts is included in a range of from 0.01 to 1 mg/ml.

In one embodiment, the compositions according to the invention are prepared by mixing commercial solutions of basal insulin, the isoelectric point of which is between 5.8 and 8.5, and commercial solutions of GLP-1 or of GLP-1 analog or derivative in volume ratios included in a range of from 10/90 to 90/10.

In one embodiment, the composition according to the invention comprises a daily dose of basal insulin and a daily dose of gut hormone.

In one embodiment, the compositions according to the invention comprise between 500 IU/ml and 40 IU/ml of basal insulin, the isoelectric point of which is between 5.8 and 8.5, and between 0.05 and 0.5 mg/ml of exenatide.

In one embodiment, the compositions according to the invention comprise between 500 IU/ml and 40 IU/ml of basal insulin, the isoelectric point of which is between 5.8 and 8.5, and from 1 to 10 mg/ml of liraglutide.

In one embodiment, the compositions according to the invention comprise between 500 IU/ml and 40 of basal insulin, the isoelectric point of which is between 5.8 and 8.5, and from 0.01 to 1 mg/ml of lixisenatide.

In one embodiment, the compositions according to the invention comprise 500 IU/ml of basal insulin, the isoelectric point of which is between 5.8 and 8.5, and from 0.05 to 0.5 mg/ml of exenatide.

In one embodiment, the compositions according to the invention comprise 500 IU/ml of basal insulin, the isoelectric point of which is between 5.8 and 8.5, and from 1 to 10 mg/ml of liraglutide.

In one embodiment, the compositions according to the invention comprise 500 IU/ml of basal insulin, the isoelectric point of which is between 5.8 and 8.5, and from 0.01 to 1 mg/ml of lixisenatide.

In one embodiment, the compositions according to the invention comprise 400 IU/ml of basal insulin, the isoelectric point of which is between 5.8 and 8.5, and from 0.05 to 0.5 mg/ml of exenatide.

In one embodiment, the compositions according to the invention comprise 400 IU/ml of basal insulin, the isoelectric point of which is between 5.8 and 8.5, and from 1 to 10 mg/ml of liraglutide.

In one embodiment, the compositions according to the invention comprise 400 IU/ml of basal insulin, the isoelectric point of which is between 5.8 and 8.5, and from 0.01 to 1 mg/ml of lixisenatide.

In one embodiment, the compositions according to the invention comprise 300 IU/ml of basal insulin, the isoelectric point of which is between 5.8 and 8.5, and from 0.05 to 0.5 mg/ml of exenatide.

In one embodiment, the compositions according to the invention comprise 300 IU/ml of basal insulin, the isoelectric point of which is between 5.8 and 8.5, and from 1 to 10 mg/ml of liraglutide.

In one embodiment, the compositions according to the invention comprise 300 IU/ml of basal insulin, the isoelectric point of which is between 5.8 and 8.5, and from 0.01 to 1 mg/ml of lixisenatide.

In one embodiment, the compositions according to the invention comprise 200 IU/ml of basal insulin, the isoelectric point of which is between 5.8 and 8.5, and from 0.05 to 0.5 mg/ml of exenatide.

In one embodiment, the compositions according to the invention comprise 200 IU/ml of basal insulin, the isoelectric point of which is between 5.8 and 8.5, and from 1 to 10 mg/ml of liraglutide.

In one embodiment, the compositions according to the invention comprise 200 IU/ml of basal insulin, the isoelectric point of which is between 5.8 and 8.5, and from 0.01 to 1 mg/ml of lixisenatide.

In one embodiment, the compositions according to the invention comprise 100 (i.e. approximately 3.6 mg/ml) of basal insulin, the isoelectric point of which is between 5.8 and 8.5, and from 0.05 to 0.5 mg/ml of exenatide.

In one embodiment, the compositions according to the invention comprise 100 IU/ml (i.e. approximately 3.6 mg/ml) of basal insulin, the isoelectric point of which is between 5.8 and 8.5, and from 1 to 10 mg/ml of liraglutide.

In one embodiment, the compositions according to the invention comprise 100 IU/ml (i.e. approximately 3.6 mg/ml) of basal insulin, the isoelectric point of which is between 5.8 and 8.5, and from 0.01 to 1 mg/ml of lixisenatide.

In one embodiment, the compositions according to the invention comprise 40 IU/ml of basal insulin, the isoelectric point of which is between 5.8 and 8.5, and from 0.05 to 0.5 mg/ml of exenatide.

In one embodiment, the compositions according to the invention comprise 40 IU/ml of basal insulin, the isoelectric point of which is between 5.8 and 8.5, and from 1 to 10 mg/ml of liraglutide.

In one embodiment, the compositions according to the invention comprise 40 RU/ml of basal insulin, the isoelectric point of which is between 5.8 and 8.5, and from 0.01 to 1 mg/ml of lixisenatide.

In one embodiment, the compositions according to the invention also comprise zinc salts at a concentration of between 0 and 5000 μM.

In one embodiment, the compositions according to the invention also comprise zinc salts at a concentration of between 0 and 4000 μM.

In one embodiment, the compositions according to the invention also comprise zinc salts at a concentration of between 0 and 3000 μM.

In one embodiment, the compositions according to the invention also comprise zinc salts at a concentration of between 0 and 2000 μM.

In one embodiment, the compositions according to the invention also comprise zinc salts at a concentration of between 0 and 1000 μM.

In one embodiment, the compositions according to the invention also comprise zinc salts at a concentration of between 50 and 600 μM.

In one embodiment, the compositions according to the invention also comprise zinc salts at a concentration of between 100 and 500 μM.

In one embodiment, the compositions according to the invention also comprise zinc salts at a concentration of between 200 and 500 μM.

In one embodiment, the compositions according to the invention also comprise buffers.

In one embodiment, the compositions according to the invention comprise buffers at concentrations of between 0 and 100 mM.

In one embodiment, the compositions according to the invention comprise buffers at concentrations of between 15 and 50 mM.

In one embodiment, the compositions according to the invention comprise a buffer chosen from the group consisting of a phosphate buffer, Tris (trishydroxymethylaminomethane) or sodium citrate.

In one embodiment, the buffer is sodium phosphate.

In one embodiment, the buffer is Tris (trishydroxymethylaminomethane).

In one embodiment, the buffer is sodium citrate,

In one embodiment, the compositions according to the invention also comprise preservatives.

In one embodiment, the preservatives are chosen from the group consisting of m-cresol and phenol, alone or as a mixture.

In one embodiment, the concentration of the preservatives is between 10 and 50 mM.

In one embodiment, the concentration of the preservatives is between 10 and 40 mM.

In one embodiment, the compositions according to the invention also comprise a surfactant.

In one embodiment, the surfactant is chosen from the group consisting of propylene glycol or polysorbate.

The compositions according to the invention can also comprise additives such as tonicity agents.

In one embodiment, the tonicity agents are chosen from the group consisting of glycerol, sodium chloride, mannitol and glycine.

The compositions according to the invention can also comprise all the excipients which are in accordance with the pharmacopeias and are compatible with the insulins used at the concentrations for use.

The invention also relates to a pharmaceutical formulation according to the invention, which is obtained by drying and/or lyophilization.

In the case of local and systemic releases, the modes of administration envisioned are intravenous, subcutaneous, intradermal or intramuscular.

Transdermal, oral, nasal, vaginal, ocular, buccal and pulmonary routes of administration are also envisioned.

The invention also relates to single-dose formulations at a pH of between 6.6 and 7.8, comprising a basal insulin, the isoelectric point of which is between 5.8 and 8.5.

The invention also relates to single-dose formulations at a pH of between 6.6 and 7.8, comprising a basal insulin, the isoelectric point of which is between 5.8 and 8,5, and a prandial insulin.

The invention also relates to single-dose formulations at a pH of between 6.6 and 7.8, comprising a basal insulin, the isoelectric point of which is between 5.8 and 8.5, and a gut hormone, as defined previously.

The invention also relates to single-dose formulations at a pH of between 6.6 and 7.8, comprising a basal insulin, the isoelectric point of which is between 5.8 and 8.5, a prandial insulin and a gut hormone, as defined previously.

The invention also relates to single-dose formulations at a pH of between 7 and 7.8, comprising a basal insulin, the isoelectric point of which is between 5.8 and 8.5.

The invention also relates to single-dose formulations at a pH of between 7 and 7.8, comprising a basal insulin, the isoelectric point of which is between 5.8 and 8.5, and a prandial insulin.

The invention also relates to single-dose formulations at a pH of between 7 and 7.8, comprising a basal insulin, the isoelectric point of which is between 5.8 and 8.5, and a gut hormone, as defined previously.

The invention also relates to single-dose formulations at a pH of between 7 and 7.8, comprising a basal insulin, the isoelectric point of which is between 5.8 and 8.5, a prandial insulin and a gut hormone, as defined previously.

In one embodiment, the single-dose formulations also comprise a substituted co-polyamino acid as defined previously.

In one embodiment, the formulations are in the form of an injectable solution.

In one embodiment, the basal insulin, the isoelectric point of which is between 5.8 and 8.5, is insulin glargine.

In one embodiment, the prandial insulin is human insulin.

In one embodiment, the insulin is a recombinant human insulin as described in the European Pharmacopeia and the US Pharmacopeia.

In one embodiment, the prandial insulin is chosen from the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

In one embodiment, the GLP-1 or GLP-1 analog or derivative is chosen from the group comprising exenatide (Byetta®), liraglutide (Victoza®), lixisenatide (Lyxumia®) or one of their derivatives.

In one embodiment, the gut hormone is exenatide.

In one embodiment, the gut hormone is liraglutide.

In one embodiment, the gut hormone is lixisenatide.

The solubilization, at a pH of between 6.6 and 7.8, of the basal insulins, the isoelectric point of which is between 5.8 and 8.5, by the substituted co-polyamino acids of formula I or IV, can be simply observed and controlled, with the naked eye, through a change in appearance of the solution.

The solubilization, at a pH of between 7 and 7.8, of the basal insulins, the isoelectric point of which is between 5.8 and 8.5, by the substituted co-polyamino acids of formula I or IV, can be simply observed and controlled, with the naked eye, through a change in appearance of the solution.

Moreover and just as importantly, the applicant was able to verify that a basal insulin, the isoelectric point of which is between 5.8 and 8.5, solubilized at a pH of between 6.6 and 7.8 in the presence of a substituted co-polyamino acid of formula I or IV, had lost nothing of its slow insulin action, either alone or in combination with a prandial insulin or a gut hormone.

The applicant was also able to verify that a prandial insulin mixed at a pH of between 6.6 and 7.8 in the presence of a co-polyamino acid of formula I or IV and of a basal insulin, the isoelectric point of which is between 5.8 and 8.5, had lost nothing of its fast insulin action.

The preparation of a composition according to the invention has the advantage of being able to be carried out by simply mixing an aqueous solution of basal insulin, the isoelectric point of which is between 5.8 and 8.5, and a substituted co-polyamino acid of formula I or IV, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a solution of prandial insulin, and a substituted co-polyamino acid of formula I or IV, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a solution of GLP-1 or a GLP-1 analog or derivative, and a substituted co-polyamino acid of formula I or IV, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a solution of prandial insulin, a solution of GLP-1 or a GLP-1 analog or derivative, and a substituted co-polyamino acid of formula I or IV, in aqueous solution or in lyophilized form. If necessary, the pH of the preparation is adjusted to pH 7.

In one embodiment, the mixture of basal insulin and substituted co-polyamino acid is concentrated by ultrafiltration before mixing with the prandial insulin in aqueous solution or in lyophilized form.

If necessary, the composition of the mixture is adjusted in terms of excipients such as glycerol, m-cresol, zinc chloride and polysorbate (Tween®) by addition of concentrated solutions of these excipients to the mixture. If necessary, the pH of the preparation is adjusted to 7.

FIG. 1 shows the results of the pharmacodynamic study obtained with a composition according to the invention in comparison with a sequential administration of the same insulins.

Represented on FIG. 1 are the mean curves and standard deviation of the mean for the sequential administrations of Humalog® (100 IU/ml) and Lantus® (100 IU/ml) (solid squares) in comparison with the administration of a composition according to the invention of co-polyamino acid 5/insulin glargine (300 IU/ml)/insulin lispro (100 IU/ml) (triangles).

EXAMPLES

Part a Synthesis of the Co-polyamino Acids

TABLE 1

List of the co-polyamino acids synthesized

| Co-polyamino acid No. | Formula | Degree of polymerization (n + m) | Degree of grafting (n/(n + m)) |
|---|---|---|---|
| 1 | (structure shown) | 40 | 9% |

TABLE 1-continued

List of the co-polyamino acids synthesized

| Co-polyamino acid No. | Formula | Degree of polymerization (n + m) | Degree of grafting (n/(n + m)) |
|---|---|---|---|
| 2 | | 200 | 10% |
| 5 | | 20 | 5% |
| 7 | | 200 | 5% |
| 3 | | 20 | 4% |

TABLE 1-continued

List of the co-polyamino acids synthesized

| Co-poly-amino acid No. | Formula | Degree of polymer-ization (n + m) | Degree of grafting (n/(n + m)) |
|---|---|---|---|
| 4 | [structure with R group, morpholine, ONa] R = [leucine-cholesterol ester structure] | 20 | 3% |
| 6 | [structure with R group, morpholine, NaO] R = [leucine-cholesterol ester structure] | 20 | 1.5% |

TABLE 1-continued

List of the co-polyamino acids synthesized

| Co-poly-amino acid No. | Formula | Degree of polymerization (n + m) | Degree of grafting (n/(n + m)) |
|---|---|---|---|
| 8 | 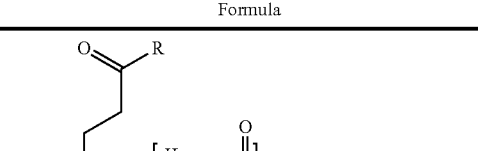 | 200 | 5% |

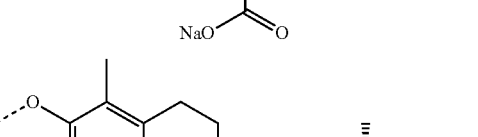

Example 1

Sodium Co-polyglutamate Modified with Dilauryl Aspartate

Co-polyamino Acid 1

A polymer of poly-γ-benzyl-L-glutamic acid with a degree of polymerization of approximately 40 is synthesized from glutamic acid γ-benzyl N-carboxyanhydride according to the process described in the publication J. Am. Chem. Soc. 2008, 130, 12562-12563 (Lu H. et al.) using N-trimethylsilylmorpholine as initiator. The degree of polymerization is estimated by $^1$H NMR by comparing the integration of the chain-end signals originating from the initiator with that of the signals originating from the repeating unit. The average degree of polymerization is 40.

To hydrolyze the benzyl esters, 10 g of polymer are refluxed for 16 h in a THF/MeOH mixture in the presence of 1N sodium hydroxide. After a return to room temperature, a white solid is isolated by filtration and analyzed by $^1$H NMR. The solid obtained is dissolved in water, acidified on an anionic Purolite resin and then lyophilized in order to generate the corresponding poly-L-glutamic acid. Dilauryl aspartate, para-toluenesulfonic acid salt is prepared according to the process described in U.S. Pat. No. 4,826,818 (Kenji M. et al.).

2 g of poly-L-glutamic acid (15.5 mmol of monomer) are solubilized in DMF and then cooled to 0° C. 0.5 g (0.8 mmol) of dilauryl aspartate, para-toluenesulfonic acid salt is suspended in DMF. 0.08 g (0.8 mmol) of triethylamine is then added to this suspension. Once the solution of polymer is at 0° C., 1.73 g (17.1 mmol) of NMM and 1.85 g (17.1 mmol) of EtOCOCl are added. After reaction for 10 min, the dilauryl aspartate solution is added and the medium is maintained at 10° C. for 45 minutes. The medium is then gradually heated to 50° C. At 30° C., 40 ml of an aqueous solution of imidazole at 100 g/l and 25 ml of water are added. After stirring for 1 h 30, the solution obtained is ultrafiltered on a 5 kD PES membrane against a solution of 0.9% NaCl, 0.01N sodium hydroxide and water. The solution is lyophilized and a $^1$H NMR analysis in deuterated trifluoroacetic acid is carried out in order to determine the degree of acid functions converted into amide of dilauryl aspartate.

According to the $^1$H NMR: the molar degree of grafting with dilauryl aspartate of the acids per monomer is 9%.

Example 2

Sodium Co-polyglutamate Modified with Alpha-tocopherol

Co-polyamino Acid 2

2 g of poly-L-glutamic acid (15.5 mmol of monomer) with a degree of polymerization of approximately 200 are synthesized by means of a process similar to that described in example 1.

The poly-L-glutamic acid is modified with alpha-tocopherol (SIGMA) according to the process described in patent FR 2,840,614 (Ping, C. U. et al.).

The solution of sodium poly-L-glutamate modified with alpha-tocopherol which is obtained is lyophilized and a $^1$H NMR analysis in deuterated trifluoroacetic acid is carried out in order to determine the degree of acid functions converted into alpha-tocopherol ester.

According to the $^1$H NMR: the molar degree of grafting with alpha-tocopherol of the acids per monomer is 10%.

Example 3

Sodium Co-polyaspartate Modified with Dilauryl Aspartate

Co-polyamino Acid 3

The dilauryl aspartate, para-toluenesulfonic acid salt is prepared according to the process described in U.S. Pat. No. 4,826,818 (Kenji M. et al.).

2 g of poly-L-aspartic acid (15.5 mmol of monomer) with a degree of polymerization of approximately 20 are synthesized by means of a process similar to that described in example 1.

The poly-L-aspartic acid is modified with dilauryl aspartate according to the process described in example 1.

The solution of sodium polyaspartate modified with dilauryl aspartate that is obtained is lyophilized and a $^1$H NMR analysis in deuterated water is carried out in order to determine the degree of acid functions converted into amide of dilauryl aspartate.

According to the $^1$H NMR: the molar degree of grafting with dilauryl aspartate of the acids per monomer is 4%.

Example 4

Sodium Co-polyaspartate Modified with Cholesteryl Leucinate

Co-polyamino Acid 4

The cholesteryl leucinate, para-toluenesulfonic acid salt is prepared according to the process described in U.S. Pat. No. 4,826,818 (Kenji M. et al.).

2 g of poly-L-aspartic add (15.5 mmol of monomer) with a degree of polymerization of approximately 20 are synthesized by means of a process similar to that described in example 1.

The poly-L-aspartic acid is modified with cholesteryl leucinate by means of a process similar to that described in example 1.

The solution of sodium poly-L-aspartate modified with cholesteryl leucinate that is obtained is lyophilized and a 91 NMR analysis in deuterated water is carried out in order to determine the degree of acid functions converted into amide of cholesteryl leucinate.

According to the $^1$H NMR: the molar degree of grafting with cholesteryl leucinate of the acids per monomer is 3%.

Example 5

Sodium Co-polyglutamate Modified with Alpha-tocopherol

Co-polyamino Acid 5

2 g of poly-L-glutamic acid (15.5 mmol of monomer) with a degree of polymerization of approximately 20 are synthesized by means of a process similar to that described in example 1.

The poly-L-glutamic acid is modified with alpha-tocopherol (SIGMA) according to the process described in patent FR 2,840,614 (Ping, C. U. et al.).

The solution of sodium poly-L-glutamate modified with alpha-tocopherol that is obtained is lyophilized and a $^1$H NMR analysis in deuterated trifluoroacetic acid is carried out in order to determine the degree of acid functions converted into alpha-tocopherol ester.

According to the $^1$H NMR: the molar degree of grafting with alpha-tocopherol of the acids per monomer is 5%.

Example 6

Sodium Co-polyglutamate Modified with Cholesteryl Leucinate

Co-polyamino Acid 6

The cholesteryl leucinate, para-toluenesulfonic acid salt is prepared according to the process described in U.S. Pat. No. 4,826,818 (Kenji M. et al.).

2 g of poly-L-glutamic acid (15.5 mmol of monomer) with a degree of polymerization of approximately 20 are synthesized by means of a process similar to that described in example 1.

The poly-L-glutamic acid is modified with the cholesteryl leucinate neutralized beforehand with triethylamine according to the process described in patent FR 2,840,614 (Ping, C. U. et al.).

The solution of sodium poly-L-glutamate modified with cholesteryl leucinate that is obtained is lyophilized and a $^1$H NMR analysis in deuterated trifluoroacetic acid is carried out in order to determine the degree of acid functions converted into alpha-tocopherol ester.

According to the $^1$H NMR: the molar degree of grafting with cholesteryl leucinate of the acids per monomer is 1.5%.

Example 7

Sodium Co-polyglutamate Modified with Alpha-tocopherol

Co-polyamino Acid 7

2 g of poly-L-glutamic acid (15.5 mmol of monomer) with a degree of polymerization of approximately 200 are synthesized by means of a process similar to that described in example 1.

The poly-L-glutamic acid is modified with alpha-tocopherol (SIGMA) according to the process described in patent FR 2,840,614 (Ping, C. U. et al.).

The solution of sodium poly-L-glutamate modified with alpha-tocopherol that is obtained is lyophilized and a $^1$H NMR analysis in deuterated trifluoroacetic acid is carried out in order to determine the degree of acid functions converted into alpha-tocopherol ester.

According to the $^1$H NMR: the molar degree of grafting with alpha-tocopherol of the acids per monomer is 5%.

Example 8

Sodium co-polyglutamate modified with Alpha-tocopherol

Co-polyamino acid 8

A polymer of poly-L-glutamic acid with a degree of polymerization of approximately 200 is synthesized from glutamic acid γ-benzyl N-carboxyanhydride using hexylamine as initiator according to the process described in patent FR 2,301,226 (Thouraud, F. et al.).

The sodium poly-L-glutamate modified with alpha-tocopherol (SIGMA) is obtained according to the process described in patent FR 2,840,614 (Ping, C. U. et al.).

The solution of sodium poly-L-glutamate modified with alpha-tocopherol that is obtained is lyophilized and a $^1$H NMR analysis in deuterated trifluoroacetic acid is carried out in order to determine the degree of acid functions converted into alpha-tocopherol ester.

According to the $^1$H NMR: the molar degree of grafting with alpha-tocopherol of the acids per monomer is 5%.

Part B Demonstration of the Properties of the Compositions According to the Invention

Example B1

Solution of Fast-acting Insulin Analog (NovoLog®) at 100 IU/ml

This solution is a commercial solution of insulin aspart sold by the company NOVO NORDISK under the name NovoLog® in the United States of America and Novorapid® in Europe. This product is a fast-acting insulin analog.

Example B2

Solution of Fast-acting Insulin Analog (Humalog®) at 100 IU/ml

This solution is a commercial solution of insulin lispro sold by the company ELI LILLY under the name Humalog®. This product is a fast-acting insulin analog.

Example B3

Solution of Fast-acting Insulin Analog (Apidra®) at 100 IU/ml

This solution is a commercial solution of insulin glulisine sold by the company SANOFI-AVENTIS under the name Apidra®. This product is a fast-acting insulin analog.

Example B4

Solution of Slow-acting Insulin Analog (Lantus®) at 100 IU/ml

This solution is a commercial solution of insulin glargine sold by the company SANOFI-AVENTIS under the name Lantus®. This product is a slow-acting insulin analog.

Example B5

Solution of Human Insulin (ActRapid®) at 100 IU/ml

This solution is a commercial solution of human insulin from NOVO NORDISK sold under the name ActRapid®. This product is a human insulin.

Example B6

Solubilization of Insulin Glargine at 100 IU/ml and at pH 7 Using a Substituted Co-polyamino Acid at the Concentration of 10 Mg/ml 20 mg of a substituted co-polyamino acid chosen from those described in Table 1 are accurately weighed out. This lyophilisate is taken up with 2 ml of the solution of insulin glargine of example B4 in order to obtain a solution of which the concentration of substituted co-polyamino acid is equal to 10 mg/ml as described in Table 2. After mechanical stirring on rollers at room temperature, the solution becomes clear. The pH of this solution is 6.3. The pH is adjusted to 7 with a 0.1 N sodium hydroxide solution. This clear solution is filtered through a membrane (0.22 μm) and is then placed at +4° C.

The solubilization test according to the above protocol was carried out with co-polyamino acids 1, 2, 3, 4, 5, 6, 7 and 8. These solutions are referenced in Table 2.

TABLE 2

Solutions according to example B6 with co-polyamino acids 1, 2, 3, 4, 5, 6, 7 and 8 at a concentration of 10 mg/ml

| Solution example B6 | Substituted co-polyamino acid | Concentration of substituted co-polyamino acid |
|---|---|---|
| B6(a) | 1 | 10 mg/ml |
| B6(b) | 2 | 10 mg/ml |
| B6(c) | 3 | 10 mg/ml |
| B6(d) | 4 | 10 mg/ml |
| B6(e) | 5 | 10 mg/ml |
| B6(f) | 6 | 10 mg/ml |
| B6(g) | 7 | 10 mg/ml |
| B6(h) | 8 | 10 mg/ml |

Generalization: Clear solutions of insulin glargine at 100 IU/ml and at pH 7 were also obtained with concentrations of substituted co-polyamino acids of 20, 40 or 60 mg/ml according to the same protocol as that described in example B6. Thus, a weight of lyophilized substituted co-polyamino acid among those described in Table 1 is accurately weighed out. This lyophilisate is taken up with the solution of insulin glargine of example B4 so as to obtain a solution of which the concentration of substituted co-polyamino acid is 20, 40 or 60 mg/ml as described in Table 3. After mechanical stirring on rollers at room temperature, the solution becomes clear. The pH of this solution is less than 7. The pH is then adjusted to 7 with a 0.1 N sodium hydroxide solution. This clear final solution is filtered through a membrane (0.22 μm) and is then placed at +4° C.

TABLE 3

Preparation of a solution of insulin glargine at 100 IU/ml and at pH 7 using a substituted co-polyamino acid at the concentration of 10, 20, 40 or 60 mg/ml

| Final concentration of substituted co-polyamino acid (mg/ml) | Weight of substituted co-polyamino acid weighed out (mg) | Added volume of the solution of insulin glargine of example B4 (ml) |
|---|---|---|
| 10 | 20 | 2 |
| 20 | 40 | 2 |
| 40 | 80 | 2 |
| 60 | 120 | 2 |

Example B7

Preparation of a Substituted Co-polyamino Acid 1/Insulin Glargine/Insulin Glulisine Composition with an Insulin Glargine/Insulin Glulisine Ratio of 75/25 at pH 7

0.25 ml of the solution of insulin glulisine of example B3 is added to 0.75 ml of the solution of substituted co-polyamino acid 1/insulin glargine prepared according to the protocol described in example B6(a), so as to form 1 ml of a composition at pH 7. The composition is clear, attesting to the good solubility of the insulin glargine and the insulin glulisine under these formulation conditions. This clear solution is filtered through 0.22 μm and is then placed at +4° C.

Example B8

Preparation of a Substituted Co-polyamino Acid 1/Insulin Glargine/Insulin Lispro Composition with an Insulin Glargine/Insulin Lispro Ratio of 75/25 at pH 7

0.25 ml of the solution of insulin lispro of example B2 is added to 0.75 ml of the solution of substituted co-polyamino acid 1/insulin glargine prepared according to the protocol described in example B6(a), so as to form 1 ml of a composition at pH 7. The composition is clear, attesting to the good solubility of the insulin glargine and of the insulin lispro under these formulation conditions. This clear solution is filtered through 0.22 µm and is then placed at +4° C.

Example B9

Preparation of a Substituted Co-polyamino Acid 1/Insulin Glargine/Insulin Aspart Composition with an Insulin Glargine/Insulin Aspart Ratio of 75/25 at pH 7

0.25 ml of the solution of insulin aspart of example 131 is added to 0.75 ml of the solution of substituted co-polyamino acid 1/insulin glargine prepared in example B6(a), so as to form 1 ml of a composition at pH 7. The composition is clear, attesting to the good solubility of the insulin glargine and of the insulin aspart under these formulation conditions. This clear solution is filtered through 0.22 µm and is then placed at +4° C.

Example B10

Preparation of a Substituted Co-polyamino Acid 1/Insulin Glargine/Human Insulin Composition with an Insulin Glargine/Human Insulin Ratio of 75/25 at pH 7

0.25 ml of the solution of human insulin of example B5 is added to 0.75 ml of the solution of substituted co-polyamino acid 1/insulin glargine prepared in example B6(a), so as to form 1 ml of a composition at pH 7. The composition is clear, attesting to the good solubility of the insulin glargine and of the human insulin under these formulation conditions. This clear solution is filtered through 0.22 µm and is then placed at +4° C.

Example B11

Preparation of a Substituted Co-polyamino Acid 1/Insulin Glargine/Insulin Glulisine Composition with an Insulin Glargine/Insulin Glulisine Ratio of 60/40 at pH 7

0.4 ml of the solution of insulin glulisine of example B3 is added to 0.6 ml of the solution of substituted co-polyamino acid 1/insulin glargine prepared in example B6(a), so as to form 1 ml of a composition at pH 7. The composition is clear, attesting to the good solubility of the insulin glargine and of the insulin glulisine under these formulation conditions. This clear solution is filtered through 0.22 µm and is than placed at +4° C.

Example B12

Preparation of a Substituted Co-polyamino Acid 1/Insulin Glargine/Insulin Glulisine Composition with an Insulin Glargine/Insulin Glulisine Ratio of 40/60 at pH 7

0.6 ml of the solution of insulin glulisine of example 133 is added to 0.4 ml of the solution of substituted co-polyamino acid 1/insulin glargine prepared in example B6(a), so as to form 1 ml of a composition at pH 7. The composition is clear, attesting to the good solubility of the insulin glargine and of the insulin glulisine under these formulation conditions. This clear solution is filtered through 0.22 prn and is then placed at +4° C.

Example B13

Precipitation of Insulin Glargine 1 ml of the solution of insulin glargine of example B4 is added to 2 ml of a solution of PBS (phosphate buffered saline) containing 20 mg/ml of BSA (bovine serum albumin). The PBS/BSA mixture simulates the composition of the subcutaneous medium. A precipitate appears, which is in good agreement with the mechanism by which insulin glargine functions (precipitation at the injection due to the increase in pH).

Centrifugation at 4000 rpm is carried out in order to separate the precipitate from the supernatant. Next, the insulin glargine is assayed in the supernatant by RP-HPLC. The result of this is that the insulin glargine is predominantly found in a precipitated form.

Example B14

Precipitation of a Substituted Co-polyamino Acid 1/Insulin Glargine Composition 1 ml of substituted co-polyamino acid 1/insulin glargine solution prepared in example B6(a) is added to 2 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Next, the insulin glargine is assayed in the supernatant by RP-HPLC. The result of this is that the insulin glargine is predominantly found in a precipitated form.

Solubilization and precipitation tests identical to those described in example B6(a) and B14 were carried out with other substituted co-polyamino acids at the same concentration of 10 mg/ml of substituted co-polyamino acid for 100 IU/ml of insulin glargine solution. The result of this is that, for all the compositions B6(b) to B6(h), the insulin glargine is predominantly found in a precipitated form after the addition of 1 ml of the composition to 2 ml of a solution of PBS containing 20 mg/ml of BSA (bovine serum albumin). The results are summarized in Table 4.

TABLE 4

Tests for solubilization and for precipitation of a substituted co-polyamino acid/insulin glargine composition

| Substituted co-polyamino acid (10 mg/ml) | Solubilization of insulin glargine | Precipitation of insulin glargine |
|---|---|---|
| 1 | yes | yes |
| 2 | yes | yes |
| 3 | yes | yes |
| 4 | yes | yes |
| 5 | yes | yes |
| 6 | yes | yes |
| 7 | yes | yes |
| 8 | yes | yes |

Example B15

Precipitation of a Substituted Co-polyamino Acid 1/Insulin Glargine/Insulin Glulisine Composition with an Insulin Glargine/Insulin Glulisine Ratio of 75/25 at pH 7

1 ml of the substituted co-polyamino acid 1/insulin glargine/insulin glulisine 75/25 composition prepared according to the protocol of example B7 is added to 2 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Next, the insulin glargine is assayed in the supernatant by RP-HPLC. The result of this is that the insulin glargine is predominantly found in a precipitated form.

Example B16

Precipitation of Various Compositions while Varying the Nature of the Substituted Co-polyamino Acid Other insulin glargine precipitation tests under the same conditions as those of example B15 were carried out in the presence of other co-polyamino acids.

The results are collated in Table 5 below and it is observed that the solubilization and the precipitation of the insulin glargine are preserved.

TABLE 5

Tests for solubilization and for precipitation of a substituted co-polyamino acid/insulin glargine/insulin glulisine 75/25 composition at pH 7

| Substituted co-polyamino acid | Solubilization of insulin glargine/insulin glulisine 75/25 | Precipitation of insulin glargine |
|---|---|---|
| 1 | yes | yes |
| 2 | yes | yes |
| 3 | yes | yes |
| 4 | yes | yes |
| 5 | yes | yes |
| 6 | yes | yes |
| 7 | yes | yes |
| 8 | yes | yes |

Example B17

Precipitation of Various Compositions while Varying the Nature of the Prandial Insulin Compositions are prepared by mixing 0.75 ml of the solution of substituted co-polyamino acid 1/insulin glargine prepared according to the protocol of example B6(a) with 0.25 ml of a prandial insulin, so as to form 1 ml of substituted co-polyamino acid 1/insulin glargine/prandial insulin composition (containing 7.5 mg/ml of substituted co-polyamino acid 1, 75 IU/ml of insulin glargine and 25 IU/ml of prandial insulin).

This composition is added to 2 ml of PBS containing 20 mg/ml of BSA (bovine serum albumin). The PBS/BSA mixture simulates the composition of the subcutaneous medium. A precipitate appears. Centrifugation at 4000 rpm is carried out in order to separate the precipitate from the supernatant. Next, the insulin glargine is assayed in the supernatant by RP-HPLC. The result of this is that the insulin glargine is found predominantly in a precipitated form. In the presence of the 4 prandial insulins tested, the insulin glargine precipitates from the PBS/BSA mixture. The results are collated in Table 6.

TABLE 6

Tests for solubilization and for precipitation of a substituted co-polyamino acid 1/insulin glargine/prandial insulin 75/25 composition

| Nature of the prandial insulin | Solubilization of insulin glargine/prandial insulin 75/25 | Precipitation of insulin glargine |
|---|---|---|
| Insulin glulisine (Apidra ®) | yes | yes |
| Insulin aspart (NovoLog ®) | yes | yes |
| Insulin lispro (Humalog ®) | yes | yes |
| Human insulin (ActRapid ®) | yes | yes |

Example B18

Preparation of a Concentrated Solution of Slow-acting Insulin Analog (Glargine)

A commercial solution of insulin glargine sold by the company SANOFI-AVENTIS under the name Lantus® is concentrated by ultrafiltration on a 3 kDa regenerated cellulose membrane (Amicon® Ultra-15 sold by the company Millipore). At the end of this ultrafiltration step, the concentration of insulin glargine is assayed in the retentate by reverse-phase liquid chromatography (RP-HPLC). The final concentration of insulin glargine is then adjusted by adding a commercial solution of glargine at 100 IU/ml, so as to obtain the desired final concentration. This process makes it possible to obtain concentrated solutions of glargine denoted $C_{insulin\ glargine}$ at various concentrations greater than 100 IU/ml, such that $C_{insulin\ glargine}$=200, 250, 300 and 333 IU/ml. The concentrated solutions are filtered through 0.22 μm and then stored at +4° C.

Example B19

Dialysis of a Commercial Solution of Fast-acting Insulin Analog (Insulin Lispro)

A commercial solution of insulin lispro sold by the company ELI LILLY under the name Humalog® is dialyzed by ultrafiltration on a 3 kDa regenerated cellulose membrane (Amicon® Ultra-15 sold by the company Millipore). The dialysis is carried out in a 1 mM phosphate buffer at pH 7. At the end of this dialysis step, the concentration $C_{insulin\ lispro}$ dialyzed in the retentate is determined by reverse-phase liquid chromatography (RP-HPLC). The dialyzed solution is stored in a freezer at −80° C.

Example B20

Lyophilization of a Solution of Fast-acting Insulin Analog (Insulin Lispro) in its Commercial Form A volume $V_{Humalog}$ of a solution of fast-acting insulin lispro at a concentration of 100 in its commercial form is placed in a lyogard® tray sterilized beforehand in an autoclave. The lyogard® tray is placed in a freezer at −80° C. for approximately 1 h and then lyophilization is carried out with the parameters of temperature 20° C. and pressure 0.31 mbar.

The resulting sterile lyophilisate is stored at room temperature.

Example B21

Lyophilization of a Commercial Solution of Fast-acting Insulin Analog (Insulin Lispro) which has been Dialyzed A volume $V_{dialyzed\ Humalog}$ of a solution of fast-acting insulin lispro obtained according to example B19 at a concentration of $C_{dialyzed\ lispro}$ is placed in a lyogard® tray sterilized beforehand in an autoclave. The lyogard® tray is placed in a freezer at −80° C. for approximately 1 h and then lyophilization is carried out with the parameters of temperature 20° C. and pressure 0.31 mbar.

The resulting sterile lyophilisate is stored at room temperature.

Example B22

Preparation of a Substituted Co-polyamino Acid/Glargine Composition at pH 7 Using Substituted Co-polyamino Acid 5, According to a Process Using Glargine in Liquid Form (in Solution) and a Co-polyamino Acid in Solid Form (Lyophilized)

A weight $w_{co-polyamino\ acid}$ of co-polyamino acid 5 is accurately weighed out. This lyophilisate is taken up with a volume $V_{glargine}$ of a concentrated solution of glargine prepared according to example B18 so as to obtain a composition having a co-polyamino acid concentration $C_{co-polyamino\ acid}$ (mg/ml)=$w_{co-polyamino\ acid}/V_{insulin\ glargine}$ and an insulin glargine concentration $C_{insulin\ glargine}$ (IU/ml). The solution is opalescent. The pH of this solution is approximately 6.3. The pH is adjusted to 7 by adding concentrated NaOH and then the solution is placed statically in an incubator at 37° C. for approximately 1 hour until complete solubilization is obtained. A volume $V_{co-polyamino\ acid/insulin\ glargine}$ of this visually clear solution is placed at +4° C.

Example B23

Preparation of a Substituted Co-polyamino Acid 5/Glargine Composition at pH 7 Using a Substituted Co-polyamino Acid 5, According to a Process Using Glargine in Liquid Form (in Solution) and a Co-polyamino Acid in Liquid Form (in Solution)

Concentrated solutions of m-cresol, glycerol and Tween® 20 are added to a stock solution of co-polyamino acid 5 at pH 7 having a concentration $C_{co-polyamino\ acid\ stock}$, so as to obtain a solution of co-polyamino acid of concentration $C_{co-polyamino\ acid\ stock/excipients}$ (mg/ml) in the presence of these excipients at contents equivalent to those described in the commercial solution Lantus® in a 10 ml bottle.

In a sterile pot, a volume $V_{Lantus}$ of a commercial solution of slow-acting insulin glargine sold under the name Lantus® at a concentration of 100 IU/ml is added to a volume $V_{co-polyamino\ acid\ stock/excipients}$ of a solution of co-polyamino acid at the concentration $C_{co-polyamino\ acid\ stock/excipients}$ (mg/ml). Cloudiness appears. The pH is adjusted to pH 7 by adding concentrated NaOH and the solution is placed statically in an incubator at 37° C. for approximately 1 h until complete solubilization is obtained. This visually clear solution is placed at +4° C.

Example B24

Preparation of a Concentrated Co-polyamino Acid 5/Glargine Composition at pH=7 Using a Substituted Co-polyamino Acid 5, According to a Process for Concentrating a Dilute Solution A dilute co-polyamino acid 5/glargine composition at pH 7 described in example B23 is concentrated by ultrafiltration on a 3 kDa regenerated cellulose membrane (Amicon® Ultra-15 sold by the company Millipore). At the end of this ultrafiltration step, the retentate is clear and the concentration of insulin glargine in the composition is determined by reverse-phase chromatography (RP-HPLC). If necessary, the concentration of insulin glargine in the composition is then adjusted to the desired value by dilution in a solution of m-cresol/glycerol/Tween®20 excipients having, for each entity, a concentration equivalent to that described in the commercial solution Lantus® (in a 10 ml bottle). This solution at pH 7, which is visually clear, and which has a glargine concentration $C_{glargine}$ (IU/ml) and a co-polyamino acid concentration $C_{co-polyamino\ acid}$ (mg/ml), is placed at +4° C.

Example B25

Preparation of a Substituted Co-polyamino Acid 5/Insulin Glargine/Insulin Lispro Composition at pH 7, from a Lyophilisate of Fast-acting Insulin Lispro in its Commercial Form (Humalog®)

A volume $V_{co-polyamino\ acid/glargine}$ of solution of co-polyamino acid 5/glargine pH 7, having a glargine concentration $C_{insulin\ glargine}$ (IU/ml) and a co-polyamino acid 5 concentration $C_{co-polyamino\ acid}$ (mg/ml), prepared according to example B22, is added to a lyophilisate of insulin lispro obtained by lyophilization of a volume $V_{insulin\ lispro}$, the preparation of which is described in example B20, such that the ratio $V_{co-polyamino\ acid\ insulin\ lispro}=100/C_{insulin\ lispro}$ where $C_{insulin\ lispro}$ is the concentration of insulin lispro (IU/ml) targeted in the composition. The solution is clear. The zinc content of the formulation is adjusted to the desired concentration $C_{zinc}$ (µM) by adding a concentrated solution of zinc chloride. The final pH is adjusted to 7 by adding concentrated NaOH or HCl.

The formulation is clear, attesting to the good solubility of glargine and insulin lispro under these formulation conditions. This solution is filtered through 0.22 µm and placed at +4° C.

Example B26

Preparation of a Substituted Co-polyamino Acid 5/Glargine/Insulin Lispro Composition at pH 7, from a Lyophilisate of a Fast-acting Insulin Lispro Obtained by Dialysis of a Commercial Solution (Humalog®)

A volume $V_{co\text{-}polyamino\ acid/insulin\ glargine}$ of solution of co-polyamino acid 5/glargine pH 7, having a glargine concentration $C_{insulin\ glargine}$ (IU/ml) and a co-polyamino acid 5 concentration $C_{co\text{-}polyamino\ acid}$ (mg/ml), prepared according to example B22, is added to a lyophilisate of insulin lispro obtained by lyophilization of a volume $V_{dialyzed\ insulin\ lispro}$, the preparation of which is described in example B21, such that the ratio $V_{co\text{-}polyamino\ acid/insulin\ glargine}/V_{dialyzed\ insulin\ lispro} = C_{dialyzed\ insulin\ lispro}/C_{insulin\ lispro}$ where $C_{dialyzed\ insulin\ lispro}$ is the concentration of insulin lispro (IU/ml) obtained at the end of the dialysis of the commercial solution, which step is described in example B19, and $C_{insulin\ lispro}$ is the concentration of insulin lispro (IU/ml) targeted in the composition. The solution is clear. The zinc content of the formulation is adjusted to the desired concentration $C_{zinc}$ (μM) by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through 022 μm and placed at +4° C.

Example B27

Preparation of a Substituted Co-polyamino Acid 5/Insulin Glargine/Insulin Lispro Composition at pH 7 Having a Glargine Concentration of 200 IU/ml and an Insulin Lispro Concentration of 66 IU/ml (Proportion as Percentage of Insulin: Glargine/Insulin Lispro 75/25)

A concentrated solution of insulin glargine at 200 IU/ml is prepared according to example B18. A composition of co-polyamino acid 5 (20 mg/ml)/insulin glargine 200 IU/ml, pH 7, is prepared from co-polyamino acid 5 and according to the method of preparation described in example B22. This co-polyamino acid 5/insulin glargine 200 IU/ml composition is added to a lyophilisate of insulin lispro obtained by lyophilization of the solution of fast-acting analog in its commercial form, according to the method of preparation described in example B25. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through 0.22 μm and placed at +4° C.

This composition is described in Table 11.

Substituted co-polyamino acid/insulin glargine/insulin lispro compositions at pH 7 were also prepared with other co-polyamino acids according to a method of preparation identical to that described in example B27 with a concentration of substituted co-polyamino acid of at most 40 mg/ml. These formulations are clear, attesting to the good solubility of the insulins glargine and lispro under these formulation conditions. These compositions result in the examples listed in Table 7.

TABLE 7

| Example | Substituted co-polyamino acid |
|---|---|
| B28 | 3 |
| B29 | 4 |
| B30 | 7 |
| B31 | 8 |

Example B32

Preparation of a Substituted Co-polyamino Add 5/Insulin Glargine/Insulin Lispro Composition at pH 7 Having a Glargine Composition of 300 IU/ml and an Insulin Lispro Concentration of 100 IU/ml (Proportion as Percentage of Insulin: Insulin Glargine/Insulin Lispro 75/25)

A concentrated solution of insulin glargine at 300 IU/ml is prepared according to example B18. A co-polyamino acid 5 (10 mg/ml)/insulin glargine 300 IU/ml composition, pH 7, is prepared from co-polyamino acid 5 and according to the method of preparation described in example B22. This co-polyamino acid 5/glargine 300 IU/ml composition is added to a lyophilisate of insulin lispro obtained by lyophilization of the solution of fast-acting analog in its commercial form, according to the method of preparation described in example B25. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through 0.22 μm and placed at +4° C. This composition is described in Table 7.

Substituted co-polyamino acid/insulin glargine/insulin lispro compositions at pH 7 were also prepared with other co-polyamino acids according to a method of preparation identical to that described in example B32 with a concentration of substituted co-polyamino acid of at most 40 mg/ml. These formulations are clear, attesting to the good solubility of the insulins glargine and lispro under these formulation conditions. These compositions result in the examples listed in Table 8.

TABLE 8

| Example | Substituted co-polyamino acid |
|---|---|
| B33 | 2 |
| B34 | 3 |
| B35 | 7 |
| B36 | 8 |

Example B37

Preparation of a Substituted Co-polyamino Acid 5/Insulin Glargine/Insulin lispro Composition at pH 7 Having an Insulin Glargine Concentration of 250 IU/ml and an Insulin Lispro Concentration of 150 IU/ml (Proportion as Percentage of Insulin: Insulin Glargine/Insulin Lispro 63/37)

A concentrated solution of insulin glargine at 250 IU/ml is prepared according to example B18. A co-polyamino acid 5

(25 mg/ml)/glargine 250 IU/ml composition at pH 7 is prepared from co-polyamino add 5 and according to the method of preparation described in example B22. This co-polyamino acid 5/glargine 250 IU/ml composition is added to a lyophilisate of insulin lispro obtained by lyophilization of the solution of fast-acting analog in its commercial form, according to the method of preparation described in example B25. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through 0.22 μm and placed at +4° C.

This composition is described in Table 11.

Substituted co-polyamino acid/insulin glargine/insulin lispro compositions at pH 7 were also prepared with other co-polyamino acids according to a method of preparation identical to that described in example B37 with a concentration of substituted co-polyamino acid of at most 40 mg/ml. These formulations are clear, attesting to the good solubility of the insulins glargine and lispro under these formulation conditions. These compositions result in the examples listed in Table 9.

TABLE 9

| Example | Substituted co-polyamino acid |
|---------|------------------------------|
| B38     | 3                            |
| B39     | 7                            |
| B40     | 8                            |

Example B41

Preparation of a Substituted Co-polyamino Acid 5/Insulin Glargine/Insulin Lispro Composition at pH 7 Having an Insulin Glargine Concentration of 333 IU/ml and an Insulin Lispro Concentration of 67 IU/ml (Proportion as Percentage of Insulin: Insulin Glargine/Insulin Lispro 83/17)

A concentrated solution of insulin glargine at 333 IU/ml is prepared according to example B18. A co-polyamino acid 5 (33 mg/ml)/insulin glargine 333 IU/ml composition, at pH 7, is prepared from co-polyamino acid 5 and according to the method of preparation described in example B22. This co-polyamino acid 5/insulin glargine 333 IU/ml composition is added to a lyophilisate of insulin lispro obtained by lyophilization of the solution of fast-acting analog in its commercial form, according to the method of preparation described in example B25. The solution is clear. The zinc content of the formulation is adjusted to the desired concentration by adding a concentrated solution of zinc chloride. The final pH is adjusted to 7 by adding concentrated NaOH or HCl.

This composition is described in Table 11.

Substituted co-polyamino acid/insulin glargine/insulin lispro compositions at pH 7 were also prepared with other co-polyamino acids according to a method of preparation identical to that described in example B41 with a concentration of substituted co-polyamino acid of at most 40 mg/ml. These formulations are clear, attesting to the good solubility of the insulins glargine and lispro under these formulation conditions. These compositions result in the examples listed in Table 10.

TABLE 10

| Example | Substituted co-polyamino acid |
|---------|------------------------------|
| B42     | 3                            |
| B43     | 7                            |
| B44     | 8                            |

Example B45

Precipitation of Various Substituted Co-polyamino Acid/Insulin Glargine/Insulin Lispro Compositions at pH 7 Having Various Concentrations of Insulins Glargine and Lispro and Various Relative Proportions of the 2 Insulins 1 ml of substituted co-polyamino acid/insulin glargine/insulin lispro composition prepared in examples B27 to B44 is added to 2 ml of a solution of PBS containing 20 mg/nn) of BSA (bovine serum albumin). The PBS/BSA mixture simulates the composition of the subcutaneous medium. A precipitate appears. Centrifugation at 4000 rpm is carried out in order to separate the precipitate from the supernatant. Next, the insulin glargine is assayed in the supernatant by RP-HPLC. The result of this is that the insulin glargine is found predominantly in a precipitated form.

The solubilization and precipitation results are summarized in Table 11.

TABLE 11

Tests for solubilization and for precipitation of various substituted co-polyamino acid/insulin glargine/insulin lispro compositions at pH 7 having various concentrations of insulin glargine and lispro and various relative proportions of the 2 insulins

| Example | Substituted co-poly-amino acid | $C_{insulin\ glargine}$ (IU/ml) | $C_{insulin\ lispro}$ (IU/ml) | $C_{insulin\ glargine}/C_{insulin\ lispro}$ (%/%) | Solubilization of insulin glargine and insulin lispro at pH 7 | Precipitation of insulin glargine |
|---------|-------------------------------|-------------------------------|------------------------------|--------------------------------------------------|--------------------------------------------------------------|-----------------------------------|
| B28     | 3                             | 200                           | 66                           | 75/25                                            | YES                                                          | YES                               |
| B29     | 4                             | 200                           | 66                           | 75/25                                            | YES                                                          | YES                               |
| B27     | 5                             | 200                           | 66                           | 75/25                                            | YES                                                          | YES                               |
| B30     | 7                             | 200                           | 66                           | 75/25                                            | YES                                                          | YES                               |
| B31     | 8                             | 200                           | 66                           | 75/25                                            | YES                                                          | YES                               |
| B33     | 2                             | 300                           | 100                          | 75/25                                            | YES                                                          | YES                               |
| B34     | 3                             | 300                           | 100                          | 75/25                                            | YES                                                          | YES                               |
| B32     | 5                             | 300                           | 100                          | 75/25                                            | YES                                                          | YES                               |
| B35     | 7                             | 300                           | 100                          | 75/25                                            | YES                                                          | YES                               |

TABLE 11-continued

Tests for solubilization and for precipitation of various substituted co-polyamino acid/insulin glargine/insulin lispro compositions at pH 7 having various concentrations of insulin glargine and lispro and various relative proportions of the 2 insulins

| Example | Substituted co-poly-amino acid | $C_{insulin\ glargine}$ (IU/ml) | $C_{insulin\ lispro}$ (IU/ml) | $C_{insulin\ glargine}/C_{insulin\ lispro}$ (%/%) | Solubilization of insulin glargine and insulin lispro at pH 7 | Precipitation of insulin glargine |
|---|---|---|---|---|---|---|
| B36 | 8 | 300 | 100 | 75/25 | YES | YES |
| B38 | 3 | 250 | 150 | 63/37 | YES | YES |
| B37 | 5 | 250 | 150 | 63/37 | YES | YES |
| B39 | 7 | 250 | 150 | 63/37 | YES | YES |
| B40 | 8 | 250 | 150 | 63/37 | YES | YES |
| B41 | 5 | 333 | 67 | 83/17 | YES | YES |
| B42 | 3 | 333 | 67 | 83/17 | YES | YES |
| B43 | 7 | 333 | 67 | 83/17 | YES | YES |
| B44 | 8 | 333 | 67 | 83/17 | YES | YES |

Part C: Demonstration of the Properties of the Compositions Comprising a GLP-1 Analog or Derivative According to the Invention Example C1

Solution of GLP-1 Analog Exenatide (Byetta®) at 0.25 mg/ml

This solution is a solution of exenatide sold by the company ELI LILLY and Company under the name Byetta®.

Example C2

Solution of GLP-1 Derivative Liraglutide g) at 6 Mg/ml

This solution is a solution of liraglutide sold by the company NOVO NORDISK under the name Victoza®.

Example C3

Preparation Of a Lantus®/Byetta® 70/30 Composition at pH 7.5

0.09 ml of the solution of exenatide of example C1 is added to 0.21 ml of the solution of insulin glargine of example B4, so as to obtain 0.3 ml of a composition of which the pH is 4.5 on mixing. The composition containing 70 IU/ml of insulin glargine and 0.075 mg/ml of exenatide is clear, attesting to the good solubility of the glargine and of the exenatide under these formulation conditions (pH 4.5). The pH is then adjusted to 7.5 with a 0.1 N sodium hydroxide solution. The composition then becomes cloudy, attesting to the poor solubility of the insulin glargine/exenatide composition at pH 7.5.

Lantus®/Byetta® 70/30 compositions were also prepared at pH 4.5-5.5-6.5-8.5 and 9.5 according to a protocol similar to that described in example C3. For each of these compositions, 0.09 ml of the solution of exenatide of example C1 is added to 0.21 ml of the solution of insulin glargine of example B4, so as to obtain 0.3 ml of a composition of which the pH is 4.5 on mixing. The composition is clear, attesting to the good solubility of the insulin glargine and of the exenatide under these formulation conditions (pH 4.5). The pH is adjusted to 5.5 or 6, 5 or 8.5 or 9.5 with a 0.1 N sodium hydroxide solution. After adjustment of the pH, the composition at pH 5.5 is slightly cloudy, the compositions at pH 6.5 and 8.5 are very cloudy and the composition at pH 9.5 is clear. These compositions are placed at +4° C. for 48 h. After 48 h at +4° C., only the composition at pH 4.5 remains clear. The visual appearance after 48 h of the Lantus®/Byetta® 70/30 compositions at various pHs is summarized in Table 12.

TABLE 12

Visual appearance after 48 h at 4° C. of the Lantus ®/Byetta ® 70/30 compositions at various pHs
Lantus ®/Byetta ® 70/30 compositions at various pHs

| pH | Visual appearance at t = 48 h |
|---|---|
| 4.5 | Clear |
| 5.5 | Presence of a precipitate |
| 6.5 | Presence of a precipitate |
| 7.5 | Presence of a precipitate |
| 8.5 | Presence of a precipitate |
| 9.5 | Presence of a precipitate |

Example C4

Preparation of a Lantus®/Victoza® 70/30 Composition at pH 7.5

0.09 ml of the solution of liraglutide of example C2 is added to 0.21 ml of the solution of insulin glargine of example B4, so as to obtain 0.3 ml of a composition of which the pH is 7 on mixing. The composition containing 70 IU/ml of insulin glargine and 1.8 mg/ml of liraglutide is cloudy, attesting to the poor solubility of the insulin glargine/liraglutide composition under these formulation conditions. The pH is adjusted to 7.5 with a 0.1 N sodium hydroxide solution. After adjustment of the pH, the composition remains cloudy. This composition is placed at +4° C. for 48 h.

Lantus®/Victoza® 70/30 compositions were also prepared at pH 4.5, 5.5, 6.5, 8.5 and 9.5 according to a protocol similar to that described in example C4. For each of these compositions, 0.09 ml of the solution of liraglutide of example C2 is added to 0.21 ml of the solution of insulin glargine of example B4, so as to obtain 0.3 ml of a composition of which the pH is 7. The composition is cloudy, attesting to the poor solubility of the insulin glargine/liraglutide composition under these formulation conditions (pH 7). The pH is adjusted to 4.5 or 5.5 or 6.5 with a 0.1 N hydrochloric acid solution or to pH 9.5 with a 0.1 N sodium hydroxide solution. After adjustment of the pH, the compositions at pH 4.5-5.5-6.5 and 8.5 are cloudy, attesting to the poor solubility of the insulin glargine/liraglutide composition under these formulation conditions. These compositions are placed at +4° C. for 48 h. After 48 h at 4° C., only the composition at pH 9.5 is clear. The visual appearance after 48 h ° of the Lantus®/Victoza® 70/30 compositions at various pHs is summarized in Table 13.

TABLE 13

Visual appearance after 48 h at 4° C. of the
Lantus ®/Victoza ® 70/30 compositions at various pHs
Lantus ®/Victoza ® 70/30 compositions at various pHs

| pH | Visual appearance at t = 48 h |
|---|---|
| 4.5 | Presence of a precipitate |
| 5.5 | Presence of a precipitate |
| 6.5 | Presence of a precipitate |
| 7.5 | Presence of a precipitate |
| 8.5 | Presence of a precipitate |
| 9.5 | Clear |

Example C5

Preparation of a Substituted Co-polyamino Acid 1/Lantus®/Byetta® Composition with a Lantus®/Byetta® Ratio of 70/30 at pH 7

0.09 ml of the solution of exenatide of example C1 is added to 0.21 ml of the solution of substituted co-polyamino acid 1/insulin glargine prepared according to the protocol of example B6(a), so as to obtain 0.3 ml of a composition at pH 5.3. The pH is adjusted to 7 with a 0.1 N sodium hydroxide solution. The composition containing 7 mg/ml of substituted co-polyamino acid 1, 70 IU/ml of insulin glargine and 0.075 mg/ml of exenatide is clear, attesting to the good solubility of the insulin glargine and of the exenatide in the presence of the substituted co-polyamino acid 1 at pH 7. This clear solution is placed at +4° C.

Generalization: Substituted co-polyamino acid/Lantus®/Byetta® compositions at pH 7 were also prepared at $V_{Lantus}/V_{Byetta}$ volume ratios of 90/10, 50/50 and 30/70 according to the same protocol as that described in example C5. Thus, a volume $V_{Byetta}$ of the solution of exenatide of example C1 is added to a volume $V_{co\text{-}polyamino\ acid/insulin\ glargine}$ of the solution of substituted co-polyamino acid/insulin glargine prepared according to the protocol of example B6, so as to obtain a composition of which the pH is adjusted to 7 with a 0.1 N sodium hydroxide solution. The compositions obtained (see Table 14) are clear, attesting to the good solubility of the insulin glargine and of the exenatide in the presence of a substituted co-polyamino acid 1 at pH 7. These clear solutions are placed at +4° C.

Example C6

Preparation of a Substituted Co-polyamino Acid 1/Lantus®/Byetta® Composition with a Lantus®/Ratio of 100/50 at pH 7

0.150 ml of the solution of exenatide of example C1 is lyophilized, then 0.3 ml of a solution of substituted co-polyamino acid/insulin glargine prepared according to the protocol of example B6(a) is added to the lyophilisate in order to obtain a composition of which the pH is adjusted to 7 with a 0.1 N sodium hydroxide solution. The composition containing 10 mg/ml of substituted co-polyamino acid 1, 100 IU/ml of insulin glargine and 0.125 mg/ml of exenatide is clear, attesting to the good solubility of the insulin glargine and of the exenatide in the presence of substituted co-polyamino acid 1 at pH 7. This clear solution is placed at +4° C.

TABLE 14

Final insulin glargine, substituted co-polyamino acid 1 and exenatide concentrations of the compositions obtained in examples C5 and C6

| $V_{Lantus}/V_{Byetta}$ | Insulin glargine mg/ml | [Substituted co-polyamino acid 1] (mg/ml) | Exenatide (mg/ml) |
|---|---|---|---|
| 100/50 | 3.5 | 10 | 0.125 |
| 90/10 | 3.15 | 9 | 0.025 |
| 70/30 | 2.45 | 7 | 0.075 |
| 50/50 | 1.75 | 5 | 0.125 |
| 30/70 | 1.05 | 3 | 0.175 |

Example C7

Preparation of a Substituted Co-polyamino Acid 1/Lantus®/Victoza® Composition with a Lantus®/Victoza® Ratio of 70/30 at pH 7

0.09 ml of the solution of liraglutide of example C2 is added to 0.21 ml of the solution of substituted co-polyamino acid/insulin glargine prepared according to the protocol of example B6(a), so as to obtain 0.3 ml of a composition at pH 7.6. The pH is adjusted to 7 with a 0.1 N hydrochloric acid solution. The composition containing 7 mg/ml of substituted co-polyamino acid 1, 70 IU/ml of insulin glargine and 1.8 mg/ml of liraglutide is clear, attesting to the good solubility of the insulin glargine and of the liraglutide in the presence of substituted co-polyamino acid 1 at pH 7. This clear solution is placed at +4° C. The final composition obtained is summarized in Table 15.

Generalization: Substituted co-polyamino acid/Lantus®/Victoza® compositions at pH 7 were also prepared at $V_{Lantus}/V_{Victoza}$ volume ratios of 90/10, 50/50 and 30/70 according to the same protocol as that described in example C7. Thus, a volume $V_{Victoza}$ of the solution of liraglutide of example C2 is added to a volume $V_{co\text{-}polyamino\ acid/insulin\ glargine}$ of the solution of substituted co-polyamino acid 1/insulin glargine at a concentration of co-polyamino acid of 40 mg/ml, prepared according to the protocol of example B6, so as to obtain a composition of which the pH is adjusted to 7 with a 0.1 N hydrochloric acid solution.

The compositions obtained (see Table 15) are clear, attesting to the good solubility of the insulin glargine and of the liraglutide in the presence of a substituted co-polyamino acid at pH 7. These clear solutions are placed at +4° C.

TABLE 15

Final insulin glargine, substituted co-polyamino acid 1 and liraglutide concentrations of the compositions obtained in example C7

| $V_{Lantus}/V_{Victoza}$ | Insulin glargine mg/ml | [Substituted co-polyamino acid 1] (mg/ml) | Liraglutide (mg/ml) |
|---|---|---|---|
| 90/10 | 3.15 | 36 | 0.6 |
| 70/30 | 2.45 | 28 | 1.8 |
| 50/50 | 1.75 | 20 | 3 |
| 30/70 | 1.05 | 12 | 4.2 |

Example C8

Preparation of a Substituted Co-polyamino Acid 1/Lantus®/Apidra®/Byetta® Composition with a Lantus®/Apidra®/Byetta® Ratio of 60/20/20 at pH 7

20 mg of lyophilized substituted co-polyamino acid 1 are accurately weighed out. This lyophilisate is taken up with 2 ml of the solution of insulin glargine of example B4. After mechanical stirring on rollers at room temperature, the solution becomes clear. The pH of this solution is 6.3. The pH is adjusted to 7 with a 0.1 N sodium hydroxide solution. 0.2 ml of the solution of exenatide of example C1 and 0.2 ml of the solution of insulin glulisine of example B3 are added to 0.6 ml of the substituted co-polyamino acid/insulin glargine solution previously prepared, so as to obtain 1 ml of a composition at pH 7. The composition containing 6 mg/ml of substituted co-polyamino acid 1, 60 IU/ml of insulin glargine, 20 IU/ml of glulisine and 0.05 mg/ml of exenatide is clear, attesting to the good solubility of the insulin glargine, of the insulin glulisine and of the exenatide in the presence of substituted co-polyamino acid 1 at pH 7. This clear solution is filtered through membrane (0.22 µm) and is then placed at +4° C.

Example C9

Precipitation of a Substituted Co-polyamino Acid/Lantus®/Byetta® Composition with a Lantus®/Byetta® Ratio of 70/30 at pH 7

0.250 ml of the substituted co-polyamino acid/Lantus®/Byetta® composition prepared according to the protocol of example C5 is added to 0.5 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. Next, the insulin glargine is assayed in the supernatant by RP-HPLC. The insulin glargine is found predominantly in a precipitated form. The result is summarized in Table 16.

Example C10

Precipitation of a Substituted Co-polyamino Acid/Lantus®/Victoza® Composition with a Lantus®/Victoza® Ratio of 70/30 at pH 7

0.250 ml of the substituted co-polyamino acid 1/Lantus®/Victoza® composition prepared according to the protocol of example C7 is added to 0.5 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Next, the insulin glargine is assayed in the supernatant by RP-HPLC. The insulin glargine is found predominantly in a precipitated form. The result is given in Table 17.

Example C11

Precipitation of Various Compositions while Varying the Nature of the Substituted Co-polyamino Acid Other tests under the same conditions as those described in examples C9 and C10 were carried out in the presence of other substituted co-polyamino acids and are respectively presented in Tables 16 and 17.

Results with at most 10 mg/ml of substituted co-polyamino acid and a Lantus®/Byetta® 70/30 composition at pH 7 are collated in Table 16 below. It is observed that the solubilization and the precipitation of the insulin glargine are preserved.

TABLES 16

Results of the solubilization and precipitation tests obtained with at most 42 or 10 mg/ml of substituted co-polyamino acid and a Lantus ®/Byetta ® 70/30 composition at pH 7

|  | Solubilization of Lantus ®/Byetta ® 70/30 at pH 7 | Precipitation of insulin glargine |
|---|---|---|
| Substituted co-polyamino acid (at most 42 mg/ml) | | |
| 8 | yes | yes |
| Substituted co-polyamino acid (at most 10 mg/ml) | | |
| 1 | yes | yes |
| 2 | yes | yes |
| 3 | yes | yes |
| 4 | yes | yes |
| 7 | yes | yes |
| 8 | yes | yes |

Results with at most 40 mg/ml of substituted co-polyamino acid and a Lantus®/Victoza® 70/30 composition at pH 7 are collated in Table 17 below. It is observed that the solubilization and the precipitation of the insulin glargine are preserved.

TABLES 17

Results of the solubilization and precipitation tests obtained with at most 40 or 42 mg/ml of substituted co-polyamino acid and a Lantus ®/Victoza ® 70/30 composition at pH 7

|  | Solubilization of Lantus ®/Victoza ® 70/30 at pH 7 | Precipitation of insulin glargine |
|---|---|---|
| Substituted co-polyamino acid, at most 42 mg/ml | | |
| 8 | yes | yes |
| Substituted co-polyamino acid, at most 40 mg/ml | | |
| 1 | yes | yes |
| 2 | yes | yes |
| 3 | yes | yes |
| 4 | yes | yes |
| 7 | yes | yes |
| 8 | yes | yes |

Example C12

Precipitation of a Substituted Co-polyamino Acid/Lantus®/Apidra®/Byetta® 60/20/20 Composition at pH 7

0.250 ml of the substituted co-polyamino acid/Lantus®/Apidra®/Byetta® composition prepared in example C8 is added to 0.5 ml of a solution of PBS containing 20 mg/ml of BSA. The PBS/BSA mixture simulates the composition of the subcutaneous medium. A precipitate appears. Centrifugation at 4000 rpm is carried out in order to separate the precipitate from the supernatant. Next, the insulin glargine is assayed in the supernatant by RP-HPLC. The insulin glargine is found predominantly in a precipitated form.

Part D: Demonstration of the Pharmacodynamic Properties of the Compositions According to the Invention Example D1

Protocol for Measuring the Pharmacodynamics of the Insulin Solutions 10 domestic pigs weighing approximately 50 kg, previously catheterized at the level of the jugular, are deprived of food for 2.5 hours before the beginning of the experiment. During the hour preceding the insulin injection, 3 blood samples are taken in order to determine the basal glucose level.

The insulin injection is given subcutaneously in the neck, under the ear of the animal using the Novopen insulin pen fitted with a 31 G needle. In the case of the double injection given as a control, an injection is given on each side of the neck.

Blood samples are then taken every 10 minutes for 1 hour and then every 30 minutes up to 2 hours, and then every hour up to 16 hours. After each sample is taken, the catheter is rinsed with a dilute heparin solution.

A drop of blood is taken in order to determine the blood glucose level by means of a glucometer.

The glucose pharmacodynamics curves are then plotted and compared.

Example D2

Results of Pharmacodynamics of the Insulin Solutions

| Examples | Insulin | Doses | Co-polyamino acid | Number of pigs |
|---|---|---|---|---|
| B2 | Double injection | Lispro 100 IU/ml | 0.05 IU/kg | — | 10 |
| B4 | | Glargine 100 IU/ml | 0.15 IU/kg | | |
| B32 | Combined injection | Lispro + glargine (100 IU/ml/300 IU/ml) | 0.2 IU/kg | 5 | 8 |

The pharmacodynamics results obtained with the formulations described in examples B2 and B4 are given in FIG. 1. According to the invention, the analysis of these curves shows (FIG. 1) that the combined insulin glargine (300 IU/ml/insulin lispro (100 IU/ml) formulation at pH 7 (triangles L) with co-polyamino add 5 of example B32 as excipient behaves similarly to the control double injection (solid squares ■) of formulation B2 and B4. The drop in blood glucose level in the first 30 minutes is similar for the two formulations, indicating that the presence of co-polyamine acid 5 does not disrupt the fast nature of the insulin lispro. Likewise, the profiles between 30 min and 4 h corresponding to the end of the fast-acting insulin and between 4 h and 16 h corresponding to the basal insulin are similar for the control double injection and for the formulation. The combination of the two insulins lispro and glargine in the presence of co-polyamino acid 5 does not therefore change the profile of these two insulins.

What is claimed is:

1. A composition in the form of an injectable aqueous solution, the pH of which is between 6.0 and 8.0, comprising at least:
(a) a basal insulin, the isoelectric point pI of which is between 5.8 and 8.5, which is insulin glargine;
(b) a co-polyamino acid bearing carboxylate charges and substituted with hydrophobic groups, chosen from the co-polyamino acids of formula I:

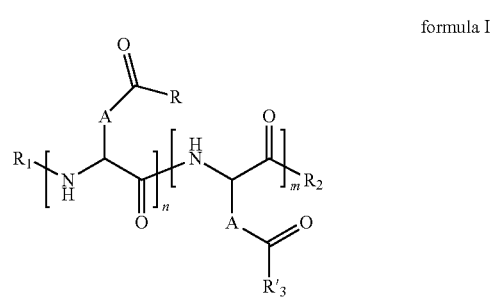

formula I in which:
A independently represents either a —$CH_2$— group (aspartic unit) or a —$CH_2$—$CH_2$— group (glutamic unit),
$R_1$ is a radical chosen from the group consisting of an H, a linear $C_2$ to $C_{10}$ acyl group, a branched $C_3$ to $C_{10}$ acyl group, a benzyl, a terminal "amino acid" unit and a pyroglutamate,
$R_2$ is an —NR'R" radical, R' and R", which may be identical or different, being chosen from the group consisting of H, linear or branched or cyclic $C_2$ to $C_{30}$ alkyls and benzyl, and said R' and R" alkyls being alkyls which can together form one or more saturated, unsaturated and/or aromatic rings which are carbon-based and/or which can comprise heteroatoms, chosen from the group consisting of O, N and S,
$R'_3$ is a radical chosen from the group consisting of the radicals of formula —$OR_3$
$R_3$ represents an H or a cationic entity chosen from the group comprising metal cations,
R is a radical derived from (i) hydrophobic alcohols and is selected from the group consisting of radicals derived from alcohols consisting of an unsaturated or saturated alkyl chain comprising from 8 to 18 carbons, cholesterol derivatives, tocopherol alcohols and alcohols bearing an aryl group, (ii) a radical of -L-R''', the R''' radical being derived from a hydrophobic acid chosen from the group consisting of fatty acids and the L radical being a linker arm comprising from 2 to 10 carbons, which is linear or branched or which can comprise heteroatoms chosen from the group consisting of N, O and S, derived from a diol, from a diamine or from an amino alcohol, or (iii) a radical of formula III or III' as defined below:

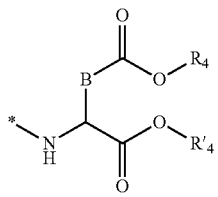

formula III

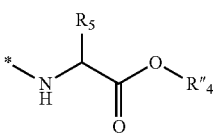

formula III' in which * indicates the site of attachment to the co-polyamino acid, and $R_4$ and $R'_4$, which may be identical or different, represent an H, a cationic entity chosen from the group comprising metal cations, an $R''_4$ radical or an $R'''_4$ radical, and at least one of $R_4$ and $R'_4$ is equal to $R''_4$, $R''_4$ is derived from hydrophobic alcohols and is selected from the group consisting of radicals derived from alcohols consisting of an unsaturated or saturated alkyl chain comprising from 8 to 18 carbons, cholesterol derivatives, tocopherol alcohols and alcohols bearing an aryl group, $R'''_4$ represents a saturated or unsaturated, linear or branched $C_1$ to $C_7$ radical which can comprise heteroatoms or a $C_1$ to $C_7$ radical which can form rings which are carbon-based or which can comprise heteroatoms, which are saturated, unsaturated and/or aromatic, said rings possibly being ortho-condensed or peri-condensed, and B independently represents either a —$CH_2$— group (aspartic unit) or a —$CH_2$—$CH_2$— group (glutamic unit), $R_5$ is a radical chosen from the group consisting of an H, a linear or branched $C_1$ to $C_4$ alkyl or a benzyl group, n/(n+m) is defined as the molar degree of grafting with hydrophobic radical of the monomeric units and is between 1 and 10 mol %, n+m represents the degree of polymerization of the co-polyamino acid, which is the average number of monomeric units per chain of co-polyamino acid, and wherein $5 \leq n+m \leq 1000$, wherein the basal insulin is soluble in the injectable aqueous solution and precipitates in subcutaneous medium and the basal insulin exhibits its biological activity and a basal action profile following injection of the aqueous solution.

2. The composition as claimed in claim 1, wherein the co-polyamino acid is chosen from the co-polyamino acids of formula IV:

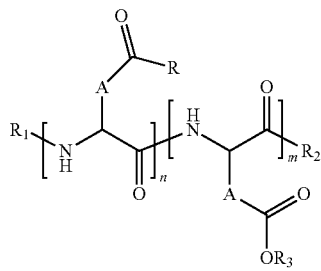

formula IV in which:

A independently represents a —$CH_2$— group (aspartic unit) or a —$CH_2$—$CH_2$— group (glutamic unit), $R_1$ is chosen from the group consisting of an H, a linear $C_2$ to $C_{10}$ acyl group, a branched $C_3$ to $C_{10}$ acyl group, a benzyl, a terminal "amino acid" unit and a pyroglutamate, $R_2$ is an —NR'R'' radical, R' and R'', which may be identical or different, being chosen from the group consisting of H, linear or branched or cyclic $C_2$ to $C_{10}$ alkyls and benzyl, and said R' and R'' alkyls being alkyls which can together form saturated, unsaturated and/or aromatic rings which are carbon-based and/or which can comprise heteroatoms, chosen from the group consisting of O, N and S, the $R_3$ groups, which may be identical or different, are chosen from the group consisting of an H or a cationic entity chosen from the group comprising metal cations, the R groups each represent, independently from one another, a radical chosen from the radicals of general formula V or V':

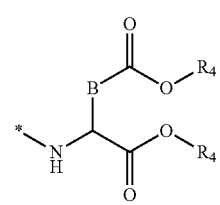

formula V

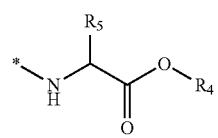

formula V' in which * indicates the site of attachment to the co-polyamino acid, and $R_4$ is equal to $R'''_4$, B independently represents a —$CH_2$— group (aspartic unit) or a —$CH_2$—$CH_2$— group (glutamic unit), $R_5$ independently represents an H, a linear or branched $C_1$ to $C_4$ alkyl or a benzyl group, or R is a radical derived from hydrophobic alcohols and is selected from the group consisting of (i) radicals derived from alcohols consisting of an unsaturated or saturated alkyl chain comprising from 8 to 18 carbons, cholesterol derivative, tocopherol alcohols and alcohols bearing an aryl group, or (ii)a radical of -L-R''', the R''' radical being derived from a hydrophobic acid chosen from the group consisting of fatty acids and the L radical being a linker arm comprising from 2 to 10 carbons, which is linear or branched or which can comprise heteroatoms selected from the group consisting N, O and S, derived from a diol, from a diamine or from an amino alcohol, n/(n+m) is defined as the molar degree of grafting with hydrophobic radical of the monomeric units, and is between 1 and 10 mol %, n+m represents the degree of polymerization of the co-polyamino acid, which is the average number of monomeric units per chain of co-polyamino acid, and wherein $5 \leq n+m \leq 1000$.

3. The composition as claimed in claim 1, wherein the co-polyamino acid is chosen from the co-polyamino acids of formula I or IV, in which the group A is a —$CH_2$— group (aspartic unit).

4. The composition as claimed in claim 3, wherein the co-polyamino acids of formula IV can also comprise monomeric units of formula VI'' and/or VI':

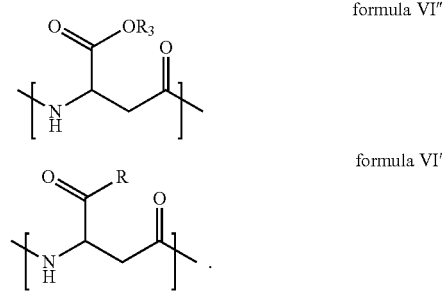

5. The composition as claimed in claim 1, wherein the co-polyamino acid is chosen from the co-polyamino acids of formula I or IV, in which the group A is a —$CH_2$—$CH_2$— group (glutamic unit).

6. The composition as claimed in claim 1, wherein the R group is a tocopheryloxy-radical.

7. The composition as claimed in claim 1, wherein $R_2$ is —N-morpholyl.

8. The composition as claimed in claim 1, wherein the $R_2$ group is a radical derived from an amino acid and is chosen from the radicals of formula VII:

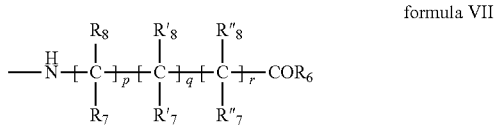

in which:

$R_6$ is —OH, —$OR_9$ or —$NHR_{10}$, and $R_7$, $R'_7$, $R''_7$, $R_8$, $R'_8$, $R''_8$, $R_9$ and $R_{10}$, which may be identical or different, independently represent an H, a linear $C_2$ to $C_{10}$ alkyl, a branched $C_3$ to $C_{10}$ alkyl or a benzyl, with $0 \leq p \leq 3$, $0 \leq q \leq 3$, $0 \leq r \leq 3$ and $1 \leq p+q+r \leq 10$.

9. The composition as claimed in claim 1, wherein the $R_4$, $R'_4$ and/or $R''_4$ groups are radicals derived from cholesterol.

10. The composition as claimed in claim 1, wherein the $R_5$ group is an isobutyl radical.

11. The composition as claimed in claim 1, wherein n+m is between 10 and 500.

12. The composition as claimed in claim 1, wherein n+m is between 15 and 250.

13. The composition as claimed in claim 1, which comprises between 40 and 500 IU/ml of basal insulin, the isoelectric point of which is between 5.8 and 8.5.

14. The composition as claimed in claim 1, wherein the concentration of substituted co-polyamino acid is at most 60 mg/ml.

15. The composition as claimed in claim 1, wherein the concentration of substituted co-polyamino acid is at most 40 mg/ml.

16. The composition as claimed in claim 1, wherein the concentration of substituted co-polyamino acid is at most 20 mg/ml.

17. The composition as claimed in claim 1, wherein the concentration of substituted co-polyamino acid is at most 10 mg/ml.

18. The composition as claimed in claim 1, which also comprises a prandial insulin.

19. The composition as claimed in claim 18, wherein the prandial insulin is human insulin.

20. The composition as claimed in claim 18, which comprises in total between 40 and 500 IU/ml of insulin with a combination of prandial insulin and basal insulin, the isoelectric point of which is between 5.8 and 8.5.

21. The composition as claimed in claim 18, wherein the proportions between the basal insulin, the isoelectric point of which is between 5.8 and 8.5, and the prandial insulin are, as a percentage, 25/75, 30/70, 40/60, 50/50, 60/40, 70/30, 80/20 or 90/10.

22. The composition as claimed in claim 1, which also comprises a gut hormone.

23. The composition as claimed in claim 22, wherein the gut hormone is chosen from the group consisting of exenatide, liraglutide and lixisenatide, their analogs or derivatives and their pharmaceutically acceptable salts.

24. The composition as claimed in claim 22, wherein the gut hormone is exenatide, its analogs or derivatives and their pharmaceutically acceptable salts.

25. The composition as claimed in claim 22, wherein the gut hormone is liraglutide, its analogs or derivatives and their pharmaceutically acceptable salts.

26. The composition as claimed in claim 22, wherein the gut hormone is lixisenatide, its analogs or derivatives and their pharmaceutically acceptable salts.

27. The composition as claimed in claim 22, wherein the concentration of gut hormone is included in a range of from 0.01 to 10 mg/ml.

28. The composition as claimed in claim 22, which comprises between 500 IU/ml and 40 IU/ml of basal insulin, the isoelectric point of which is between 5.8 and 8.5, and from 0.05 to 0.5 mg/ml of exenatide.

29. The composition as claimed in claim 22, which comprises between 500 IU/ml and 40 IU/ml of basal insulin, the isoelectric point of which is between 5.8 and 8.5, and from 1 to 10 mg/ml of liraglutide.

30. The composition as claimed in claim 22, which comprises between 500 IU/ml and 40 IU/ml of basal insulin, the isoelectric point of which is between 5.8 and 8.5, and from 0.01 to 1 mg/ml of lixisenatide.

* * * * *

UNITED STATES PATENT AND TRADEMARK OFFICE
CERTIFICATE OF CORRECTION

PATENT NO. : 9,198,971 B2
APPLICATION NO. : 13/737353
DATED : December 1, 2015
INVENTOR(S) : Olivier Soula It is certified that error appears in the above-identified patent and that said Letters Patent is hereby corrected as shown below:

In the specification

In Col. 5, line 58, "between 5.6 and 3.5," should be ---between 5.8 and 8.5,---.

In Col. 7, line 1, "or ped-condensed," should be ---or peri-condensed,---.

In Col. 7, line 44, "—$CH_1$—" should be --- —$CH_2$— ---.

In Col. 9, line 65, "the co-polyamino add" should be ---the co-polyamino acid---.

In Col. 13, line 36, "the co-polyamino adds" should be ---the co-polyamino acid---.

In Col. 14, line 16, "the dials are chosen" should be ---the diols are chosen---.

In Col. 14, line 28, "alaninol, valinol, leucinal," should be ---alaninol, valinol, leucinol,---.

In Col. 14, line 57, "—OR," should be --- —$OR_9$,---.

In Col. 17, line 37, "between 5.8 and 6.5." should be ---between 5.8 and 8.5.---.

In Col. 17, line 48, "between 5.8 and 6.5," should be ---between 5.8 and 8.5,---.

In Col. 18, line 33, "between 5.6 and 8.5." should be ---between 5.8 and 8.5.---.

In Col. 18, line 37, "between 5.6 and 8.5." should be ---between 5.8 and 8.5.---.

In Col. 18, line 43, "700 of insulin" should be ---700 IU/ml of insulin---.

In Col. 18, line 47, "600 of insulin" should be ---600 IU/ml of insulin---.

Signed and Sealed this
Seventeenth Day of May, 2016

Michelle K. Lee
*Director of the United States Patent and Trademark Office*

In the specification

In Col. 19, line 40, "constituent amino add" should be ---constituent amino acid---.

In Col. 20, line 12, "500 IU/ml and 40" should be ---500 IU/ml and 40 IU/ml---.

In Col. 20, line 61, "comprise 100" should be ---comprise 100 IU/ml---.

In Col. 21, line 14, "comprise 40 RU/ml" should be ---comprise 40 IU/ml---.

In Col. 21, line 53, "buffer is sodium citrate," should be ---buffer is sodium citrate.---.

In Col. 27, line 20, the chemical formula for co-polyamino acid No. 6 should be represented as:

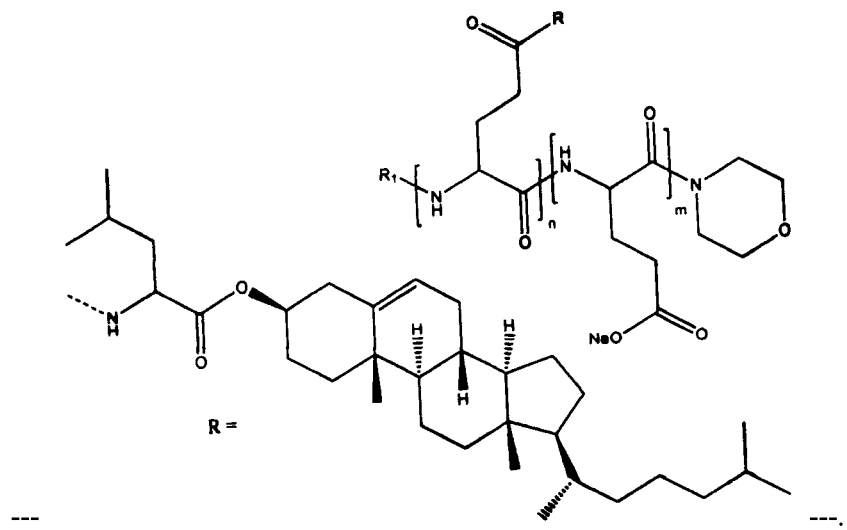

---                                                                                           ---.

In Col. 29, line 66, "100 gil" should be ---100 g/l---.

In Col. 31, line 37, "and a 91" should be ---and a $^1$H---.

In Col. 33, line 56, "the Concentration of 10 Mg/ml" should be ---the Concentration of 10 mg/ml---.

In Col. 35, line 26, "example 131" should be ---example B1---.

In Col. 36, line 9, "example 133" should be ---example B3---.

In Col. 36, line 16, "through 0.22 prn" should be ---through 0.22 µm---.

In Col. 39, line 13, "concentration of 100" should be ---concentration of 100 IU/ml---.

In Col. 41, line 31, "filtered through 022" should be ---filtered through 0.22---.

CERTIFICATE OF CORRECTION (continued)
U.S. Pat. No. 9,198,971 B2

In Col. 42, line 15, "Co-polyamino Add" should be ---Co-polyamino Acid---.

In Col. 43, line 2, "co-polyamino add" should be ---co-polyamino acid---.

In Col. 44, line 39, "containing 20 mg/nn" should be ---containing 20 mg/ml---.

In Col. 45, line 35, "Liraglutide g)" should be ---Liraglutide (Victoza®)---.

In Col. 45, line 36, "Mg/ml" should be ---mg/ml---.

In Col. 47, line 4, "after 48 h°" should be ---after 48 h---.

In Col. 51, line 54, "(300 IU/ml/insu-" should be ---(300 IU/ml)/insu- ---.

In Col. 51, line 55, "(triangles L)" should be ---(triangles Δ)---.

In the claims

In Col. 54, line 67, "or (ii)a" should be ---or (ii) a---.

In Col. 55, line 43, "tocopheryloxy-radical." should be ---tocopheryloxy- radical.---.